United States Patent
Keaney et al.

(10) Patent No.: US 11,993,586 B2
(45) Date of Patent: May 28, 2024

(54) CRYSTALLINE FORMS OF POTASSIUM CHANNEL MODULATORS

(71) Applicant: Novartis AG, Basel (CH)

(72) Inventors: Gregg F. Keaney, Lexington, MA (US); Jun Xu, Cranbury, NJ (US); Wenfeng Xue, Cranbury, NJ (US)

(73) Assignee: Novartis AG, Basel (CH)

( * ) Notice: Subject to any disclaimer, the term of this patent is extended or adjusted under 35 U.S.C. 154(b) by 549 days.

(21) Appl. No.: 17/287,907

(22) PCT Filed: Oct. 21, 2019

(86) PCT No.: PCT/US2019/057203
§ 371 (c)(1),
(2) Date: Apr. 22, 2021

(87) PCT Pub. No.: WO2020/086456
PCT Pub. Date: Apr. 30, 2020

(65) Prior Publication Data
US 2021/0395229 A1 Dec. 23, 2021

Related U.S. Application Data

(60) Provisional application No. 62/748,632, filed on Oct. 22, 2018.

(51) Int. Cl.
*C07D 403/04* (2006.01)

(52) U.S. Cl.
CPC ........ *C07D 403/04* (2013.01); *C07B 2200/13* (2013.01)

(58) Field of Classification Search
CPC .................... C07D 403/04; C07B 2200/13
See application file for complete search history.

(56) References Cited

U.S. PATENT DOCUMENTS

| | | | |
|---|---|---|---|
| 3,040,047 A | 6/1962 | Kenzo | |
| 4,992,150 A | 2/1991 | Igarashi et al. | |
| 5,250,530 A | 10/1993 | Giencke et al. | |
| 6,225,052 B1 | 5/2001 | Batz et al. | |
| 7,767,777 B2 | 8/2010 | Buesing et al. | |
| 7,919,046 B2 | 4/2011 | Delapierre et al. | |
| 8,106,217 B2 | 1/2012 | Ignatyev et al. | |
| 8,222,262 B2 | 7/2012 | Eriksen et al. | |
| 8,252,806 B2 | 8/2012 | Eriksen et al. | |
| 8,362,024 B2 | 1/2013 | Eriksen et al. | |
| 8,563,552 B2 | 10/2013 | Hanyu et al. | |
| 8,586,573 B2 | 11/2013 | Dubois et al. | |
| 9,050,266 B2 | 6/2015 | Poinsard et al. | |
| 9,321,727 B2 | 4/2016 | Bissantz et al. | |
| 9,340,544 B2 | 5/2016 | Eriksen et al. | |
| 9,505,720 B2 | 11/2016 | Poinsard et al. | |
| 9,975,886 B1 | 5/2018 | Amrutkar et al. | |
| 10,351,553 B2 | 7/2019 | Amrutkar et al. | |
| 10,717,728 B2 | 7/2020 | Amrutkar et al. | |
| 10,774,064 B2 | 9/2020 | Eriksen et al. | |
| 2002/0137747 A1 | 9/2002 | Moriarty et al. | |
| 2004/0229864 A1 | 11/2004 | Bourrain et al. | |
| 2005/0113382 A1 | 5/2005 | Jahangir et al. | |
| 2005/0277640 A1 | 12/2005 | Dixon et al. | |
| 2006/0069066 A1 | 3/2006 | Eldar-Finkelman et al. | |
| 2006/0156481 A1 | 7/2006 | Lim | |
| 2006/0281712 A1 | 12/2006 | Yen et al. | |
| 2007/0135437 A1 | 6/2007 | Benjamin et al. | |
| 2008/0221103 A1 | 9/2008 | Sharma et al. | |
| 2008/0249097 A1 | 10/2008 | Daifuku et al. | |
| 2008/0255183 A1 | 10/2008 | Arnould et al. | |
| 2008/0275045 A1 | 11/2008 | Eriksen et al. | |
| 2009/0036475 A1 | 2/2009 | Eriksen et al. | |

(Continued)

FOREIGN PATENT DOCUMENTS

| | | |
|---|---|---|
| CL | 2006000460 A1 | 9/2006 |
| CL | 2007002455 A1 | 4/2008 |

(Continued)

OTHER PUBLICATIONS

U.S. Appl. No. 15/749,325, filed Jan. 31, 2018, U.S. Pat. No. 10,774,064, Issued.
U.S. Appl. No. 16/923,247, filed Jul. 8, 2020, Abandoned.
U.S. Appl. No. 17/177,630, filed Feb. 17, 2021, Abandoned.
U.S. Appl. No. 17/487,815, filed Sep. 28, 2021, Pending.
U.S. Appl. No. 15/617,091, filed Jun. 8, 2018, 2017-0355708, Abandoned.
U.S. Appl. No. 15/877,910, filed Jan. 23, 2018, U.S. Pat. No. 9,975,886, Issued.
U.S. Appl. No. 15/938,292, filed Mar. 28, 2018, U.S. Pat. No. 10,351,553, Issued.

(Continued)

*Primary Examiner* — Bahar Craigo
*Assistant Examiner* — Manahil Mirghani Ali Abdalhameed
(74) *Attorney, Agent, or Firm* — McCarter & English, LLP

(57) ABSTRACT

Provided herein are crystalline and amorphous forms of a compound having structural formula (1). Also provided are pharmaceutical compositions comprising the crystalline and amorphous forms, methods for their manufacture, and uses thereof for treating a variety of diseases, disorders or conditions, associated with potassium channels.

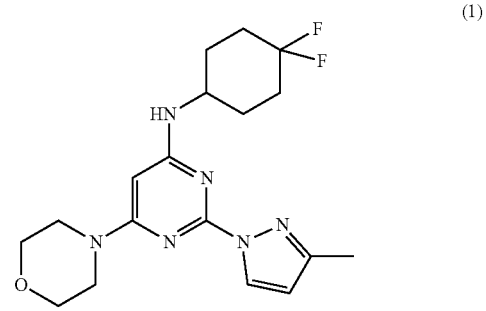

(1)

13 Claims, 19 Drawing Sheets

(56) References Cited

U.S. PATENT DOCUMENTS

| | | |
|---|---|---|
| 2009/0068634 A1 | 3/2009 | Cerda |
| 2009/0143302 A1 | 6/2009 | Yen et al. |
| 2009/0253717 A1 | 10/2009 | Brown et al. |
| 2009/0306102 A1 | 12/2009 | Eriksen et al. |
| 2009/0325989 A1 | 12/2009 | Eriksen et al. |
| 2010/0324273 A1 | 12/2010 | Singer et al. |
| 2011/0144140 A1 | 6/2011 | Eriksen et al. |
| 2011/0152292 A1 | 6/2011 | Rayner-Branes et al. |
| 2011/0224155 A1 | 9/2011 | Tachdjian et al. |
| 2011/0230484 A1 | 9/2011 | Eriksen et al. |
| 2011/0257196 A1 | 10/2011 | Lu et al. |
| 2012/0004246 A1 | 1/2012 | Eriksen et al. |
| 2012/0046301 A1 | 2/2012 | Frank et al. |
| 2012/0071524 A1 | 3/2012 | Lu et al. |
| 2012/0165309 A1 | 6/2012 | Takahashi et al. |
| 2012/0202806 A1 | 8/2012 | Durrenberger et al. |
| 2013/0197049 A1 | 8/2013 | Li et al. |
| 2013/0338066 A1 | 12/2013 | Boehme et al. |
| 2014/0275024 A1 | 9/2014 | Maxwell et al. |
| 2015/0291515 A1 | 10/2015 | Uerdingen et al. |
| 2015/0343216 A1 | 12/2015 | Poelzin et al. |
| 2016/0155959 A1 | 6/2016 | Kaiser et al. |
| 2016/0237069 A1 | 8/2016 | Beaton et al. |
| 2017/0015871 A1 | 1/2017 | Wutti et al. |
| 2017/0299609 A1 | 10/2017 | Elbasiouny |
| 2017/0355708 A1 | 12/2017 | Jefson et al. |
| 2018/0207138 A1 | 7/2018 | Amrutkar et al. |
| 2021/0380571 A1 | 12/2021 | Amrutkar et al. |
| 2021/0395229 A1 | 12/2021 | Keaney et al. |

FOREIGN PATENT DOCUMENTS

| | | |
|---|---|---|
| CN | 101115736 A | 1/2008 |
| CN | 101684098 A | 3/2010 |
| CN | 102177154 A | 9/2011 |
| CN | 102731492 A | 10/2012 |
| CN | 103626741 A | 3/2014 |
| CN | 106349156 A | 1/2017 |
| DE | 3634341 A1 | 5/1987 |
| DE | 4034762 A1 | 5/1992 |
| DE | 102012006896 A1 | 10/2013 |
| EP | 353123 A1 | 1/1990 |
| EP | 407899 A2 | 1/1991 |
| EP | 646648 A1 | 4/1995 |
| EP | 1270551 A1 | 1/2003 |
| EP | 1506967 A1 | 2/2005 |
| EP | 2042570 A1 | 4/2009 |
| EP | 2746373 A2 | 6/2014 |
| EP | 2746374 A2 | 6/2014 |
| ES | 2469290 A1 | 6/2014 |
| FR | 2904316 A1 | 2/2008 |
| GB | 2263639 A | 8/1993 |
| JP | 54-147921 A | 11/1979 |
| JP | H02282251 A | 11/1990 |
| JP | H11158073 A | 6/1999 |
| JP | H11282132 A | 10/1999 |
| JP | 2000-072695 A | 3/2000 |
| JP | 2000-075449 A | 3/2000 |
| JP | 2007-091649 A | 4/2007 |
| JP | 2013-020223 A | 1/2013 |
| JP | 2013-061465 A | 4/2013 |
| JP | 2013-125180 A | 6/2013 |
| KR | 20120018236 A | 3/2012 |
| TW | I322686 B | 4/2010 |
| TW | I552750 B | 10/2016 |
| WO | 1989/11279 A1 | 11/1989 |
| WO | 1993/25550 A1 | 12/1993 |
| WO | 1995/00478 A1 | 1/1995 |
| WO | 1998/06709 A1 | 2/1998 |
| WO | 1998/17630 A1 | 4/1998 |
| WO | 2001/017942 A1 | 3/2001 |
| WO | 2001/32170 A1 | 5/2001 |
| WO | 2002/00217 A1 | 1/2002 |
| WO | 2002/030358 A2 | 4/2002 |
| WO | 2002/046172 A2 | 6/2002 |
| WO | 2002/055012 A2 | 7/2002 |
| WO | 2002/055013 A2 | 7/2002 |
| WO | 2002/055014 A2 | 7/2002 |
| WO | 2002/064096 A2 | 8/2002 |
| WO | 2003/053933 A1 | 7/2003 |
| WO | 2003/075828 A2 | 9/2003 |
| WO | 2004/000820 A2 | 12/2003 |
| WO | 2004/000833 A1 | 12/2003 |
| WO | 2004/017920 A2 | 3/2004 |
| WO | 2004/018452 A1 | 3/2004 |
| WO | 2005/035507 A2 | 4/2005 |
| WO | 2005/037826 A1 | 4/2005 |
| WO | 2005/075461 A1 | 8/2005 |
| WO | 2005/095357 A2 | 10/2005 |
| WO | 2005/112938 A2 | 12/2005 |
| WO | 2006/014136 A1 | 2/2006 |
| WO | 2006/034473 A2 | 3/2006 |
| WO | 2006/040113 A2 | 4/2006 |
| WO | 2006/048330 A1 | 5/2006 |
| WO | 2006/053109 A1 | 5/2006 |
| WO | 2006/065590 A2 | 6/2006 |
| WO | 2006/074057 A2 | 7/2006 |
| WO | 2006/077364 A1 | 7/2006 |
| WO | 2006/077365 A1 | 7/2006 |
| WO | 2006/077366 A1 | 7/2006 |
| WO | 2006/077367 A1 | 7/2006 |
| WO | 2006/077412 A1 | 7/2006 |
| WO | 2006/100212 A1 | 9/2006 |
| WO | 2006/128563 A1 | 12/2006 |
| WO | 2006/138266 A2 | 12/2006 |
| WO | 2007/015064 A1 | 2/2007 |
| WO | 2007/031185 A1 | 3/2007 |
| WO | 2007/042810 A1 | 4/2007 |
| WO | 2007/048924 A1 | 5/2007 |
| WO | 2007/062222 A2 | 5/2007 |
| WO | 2007/070556 A2 | 6/2007 |
| WO | 2007/070600 A2 | 6/2007 |
| WO | 2007/089735 A2 | 8/2007 |
| WO | 2007/128462 A1 | 11/2007 |
| WO | 2008/005538 A2 | 1/2008 |
| WO | 2008/016300 A2 | 2/2008 |
| WO | 2008/024398 A2 | 2/2008 |
| WO | 2008/024974 A1 | 2/2008 |
| WO | 2008/052861 A2 | 5/2008 |
| WO | 2008/064218 A2 | 5/2008 |
| WO | 2008/070661 A1 | 6/2008 |
| WO | 2008/090382 A1 | 7/2008 |
| WO | 2008/098058 A1 | 8/2008 |
| WO | 2008/104994 A2 | 9/2008 |
| WO | 2008/116909 A1 | 10/2008 |
| WO | 2008/116910 A1 | 10/2008 |
| WO | 2008/116911 A1 | 10/2008 |
| WO | 2008/116912 A1 | 10/2008 |
| WO | 2008/116914 A1 | 10/2008 |
| WO | 2008/154221 A2 | 12/2008 |
| WO | 2009/017838 A2 | 2/2009 |
| WO | 2009/099193 A1 | 8/2009 |
| WO | 2009/105881 A1 | 9/2009 |
| WO | 2009/120094 A2 | 10/2009 |
| WO | 2009/125870 A1 | 10/2009 |
| WO | 2009/150462 A1 | 12/2009 |
| WO | 2009/152902 A2 | 12/2009 |
| WO | 2010/000396 A1 | 1/2010 |
| WO | 2010/015037 A1 | 2/2010 |
| WO | 2010/020432 A2 | 2/2010 |
| WO | 2010/026087 A1 | 3/2010 |
| WO | 2010/034707 A1 | 4/2010 |
| WO | 2010/048149 A2 | 4/2010 |
| WO | 2010/052569 A2 | 5/2010 |
| WO | 2010/068863 A2 | 6/2010 |
| WO | 2010/072823 A1 | 7/2010 |
| WO | 2010/120994 A2 | 10/2010 |
| WO | 2010/129053 A2 | 11/2010 |
| WO | 2010/151711 A1 | 12/2010 |
| WO | 2010/151797 A2 | 12/2010 |
| WO | 2011/004162 A2 | 1/2011 |
| WO | 2011/008931 A2 | 1/2011 |
| WO | 2011/018894 A1 | 2/2011 |
| WO | 2011/026579 A1 | 3/2011 |

(56) References Cited

FOREIGN PATENT DOCUMENTS

| WO | 2011/026835 A1 | 3/2011 | |
| --- | --- | --- | --- |
| WO | 2011/029832 A1 | 3/2011 | |
| WO | 2011/060304 A2 | 5/2011 | |
| WO | 2011/077043 A2 | 6/2011 | |
| WO | 2011/079343 A2 | 7/2011 | |
| WO | 2011/109059 A1 | 9/2011 | |
| WO | 2011/143365 A1 | 11/2011 | |
| WO | 2012/009258 A2 | 1/2012 | |
| WO | 2012/016133 A2 | 2/2012 | |
| WO | 2012/022487 A1 | 2/2012 | |
| WO | 2012/042005 A1 | 4/2012 | |
| WO | 2012/050884 A2 | 4/2012 | |
| WO | 2012/052540 A1 | 4/2012 | |
| WO | 2012/080729 A2 | 6/2012 | |
| WO | 2012/088438 A1 | 6/2012 | |
| WO | 2012/109343 A2 | 8/2012 | |
| WO | 2012/129562 A2 | 9/2012 | |
| WO | 2012/154880 A1 | 11/2012 | |
| WO | 2012/154967 A1 | 11/2012 | |
| WO | 2012/163489 A1 | 12/2012 | |
| WO | 2012/167171 A2 | 12/2012 | |
| WO | 2013/033240 A1 | 3/2013 | |
| WO | 2013/120040 A1 | 8/2013 | |
| WO | 2013/178816 A1 | 12/2013 | |
| WO | 2013/190212 A1 | 12/2013 | |
| WO | 2014/017938 A2 | 1/2014 | |
| WO | 2014/031681 A1 | 2/2014 | |
| WO | 2014/031872 A2 | 2/2014 | |
| WO | 2014/045031 A1 | 3/2014 | |
| WO | 2014/067603 A1 | 5/2014 | |
| WO | 2014/078733 A1 | 5/2014 | |
| WO | 2014/107622 A1 | 7/2014 | |
| WO | 2014/108487 A1 | 7/2014 | |
| WO | 2014/134141 A1 | 9/2014 | |
| WO | 2014/165827 A1 | 10/2014 | |
| WO | 2014/177060 A1 | 11/2014 | |
| WO | 2015/000548 A1 | 1/2015 | |
| WO | 2015/003640 A1 | 1/2015 | |
| WO | 2015/011284 A2 | 1/2015 | |
| WO | 2015/013715 A2 | 1/2015 | |
| WO | 2015/031725 A1 | 3/2015 | |
| WO | 2015/049034 A1 | 4/2015 | |
| WO | 2015/061247 A2 | 4/2015 | |
| WO | 2015/069752 A1 | 5/2015 | |
| WO | 2015/079028 A1 | 6/2015 | |
| WO | 2015/084936 A1 | 6/2015 | |
| WO | 2015/154039 A2 | 10/2015 | |
| WO | 2016/058544 A1 | 4/2016 | |
| WO | 2016/128772 A1 | 8/2016 | |
| WO | 2017/044889 A1 | 3/2017 | |
| WO | 2017/210545 A1 | 12/2017 | |
| WO | WO-2017210545 A1 * | 12/2017 | ............. A61P 25/00 |

OTHER PUBLICATIONS

U.S. Appl. No. 16/431,212, filed Jun. 4, 2019, U.S. Pat. No. 10,717,728, Issued.
U.S. Appl. No. 16/897,743, filed Jun. 10, 2020, Abandoned.
U.S. Appl. No. 17/150,230, filed Jan. 15, 2021, 2021-0380571, Published.
U.S. Appl. No. 17/458,769, filed Aug. 27, 2021, Pending.
U.S. Appl. No. 15/877,918, filed Jan. 23, 2018, 2018-0207138, Abandoned.
U.S. Appl. No. 17/177,630, filed Feb. 17, 2021, Pending.
U.S. Appl. No. 17/150,230, filed Jan. 15, 2021, Pending.
Kummerer, Pharmaceuticals in the Environment. Annu Rev Environ Resour. 2010;35:57-75.
Sarma et al., Solid forms of pharmaceuticals: Polymorphs, salts and cocrystals. Korean Journal of Chemical Engineering. 2011;28:315-322.
Variankaval et al., From form to function: Crystallization of active pharmaceutical ingredients. AlChE Journal. Jul. 2008;54(7):1682-1688.
Addolorato et al., Novel therapeutic strategies for alcohol and drug addiction: focus on GABA, ion channels and transcranial magnetic stimulation. Neuropsychopharmacology. Jan. 2012;37(1):163-77.
Bagal et al., Ion channels as therapeutic targets: a drug discovery perspective. J Med Chem. Feb. 14, 2013;56 (3):593-624.
Boucherat et al., Potassium channels in pulmonary arterial hypertension. Eur Respir J. Oct. 2015;46(4):1167-77.
Caira, Crystalline Polymorphism of Organic Compounds. Topics in Current Chemistry. Springer Verlag, Berlin Heidelberg. vol. 198, pp. 163-208.
Cao et al., Modulation of recombinant and native neuronal SK channels by the neuroprotective drug riluzole. Eur J Pharmacol. Aug. 2, 2002;449(1-2):47-54.
Cueni et al., T-type Ca2+ channels, SK2 channels and SERCAs gate sleep-related oscillations in thalamic dendrites. Nat Neurosci. Jun. 2008;11(6):683-92.
Kanai et al., Altered axonal excitability properties in amyotrophic lateral sclerosis: impaired potassium channel function related to disease stage. Brain. Apr. 2006; 129(Pt 4):953-62.
Kasumu et al., Novel Selective positive modulator of calcium-activated potassium channels exerts beneficial effects in a mouse model of spinocerebellar ataxia type 2. Chem Biol. Oct. 26, 2012;19(10):1340-53.
Kobayashi et al., Effects of nicorandil, a potassium channel opener, on idiopathic ventricular tachycardia. J Am Coll Cardiol. Nov. 1998;32(5):1377-83.
Lei et al., Alterations of A-type potassium channels in hippocampal neurons after traumatic brain injury. J Neurotrauma. Jan. 20, 2012;29(2):235-45.
Liu et al., Modulation of the activity of dopaminergic neurons by SK channels: a potential target for the treatment of Parkinson's disease? Neurosci Bull. Jun. 2010;26(3):265-71.
Nilsson et al., Structural basis for the inhibition of Mycobacterium tuberculosis glutamine synthetase by novel ATP-competitive inhibitors. J Mol Biol. Oct. 23, 2009;393(2):504-13.
Rahimi Shourmasti et al., Effects of riluzole on harmaline induced tremor and ataxia in rats: biochemical, histological and behavioral studies. Eur J Pharmacol. Nov. 15, 2012;695(1-3):40-7.
Tano et al., Calcium-activated potassium channels in ischemia reperfusion: a brief update. Front Physiol. Oct. 6, 2014;5:381. 5 pages.
Waszkielewicz et al., Ion channels as drug targets in central nervous system disorders. Curr Med Chem. 2013;20(10):1241-85.
Windler et al., The Ca21-dependent K1-channel KCa3.1 as a therapeutic target in cardiovascular disease. European Heart Journal Supplements. 2014;16(Suppl A):A30-A32.
Yi et al., Down-regulation of the Small-Conductance Calcium-Activated Potassium Channels in Diabetic Mouse Atria. JBC Papers in Press, published on Jan. 20, 2015 as Manuscript M114.607952, retrieved online at: http://www.jbc.org/cgi/doi/10.1074/jbc.M114.607952. 21 pages, (2015).
Zaki et al., Nicorandil—A Potassium Channel Opener-Ameliorates Overactive Bladder Induced by Type-1 Diabetes in the Male Albino Rats. Med J Cairo Univ. Dec. 2015;83(2):325-332.
Braga et al., Crystal Polymorphism and Multiple Crystal Forms. Molecular Networks. Structure and Bonding, vol. 132. D.M.P. Mingos (Ed.), Springer. pp. 87-95, Jan. 1, 2009.
Hilfiker et al., Relevance of Solid-state Properties for Pharmaceutical Products. Polymorphism: in the Pharmaceutical Industry. Wiley-VCH Verlag GmbH & Co. KGaA. Chapter 1, 19 pages. Feb. 6, 2006.

* cited by examiner

CRYSTALLINE FORMS OF POTASSIUM CHANNEL MODULATORS

RELATED APPLICATIONS

This application is a 35 U.S.C. § 371 national stage filing of International Application No. PCT/US2019/057203, filed Oct. 21, 2019, which claims priority to U.S. Provisional Application No. 62/748,632 filed Oct. 22, 2018. The entire contents of each of the forgoing applications are incorporated herein by reference.

BACKGROUND

Among the ion channels, potassium channels are the most prevalent and diverse, being found in a variety of animal cells such as nervous, muscular, glandular, immune, reproductive, and epithelial tissue. These channels allow the flow of potassium in and/or out of the cell under certain conditions. These channels are regulated, e.g., by calcium sensitivity, voltage-gating, second messengers, extracellular ligands, and ATP-sensitivity.

Dysfunction of potassium channels and dysfunction from other causes which influence these potassium channels are known to generate loss of cellular control, altered physiological function, and disease conditions. Because of their ability to modulate ion channel function and/or regain ion channel activity, potassium channel modulators are being used in the pharmacological treatment of a wide range of pathological diseases and have the potential to address an even wider variety of therapeutic indications.

The small conductance calcium-activated potassium channels (SK channel) are a subfamily of $Ca^{2+}$ activated $K^+$ channels and the SK channel family contains 4 members—SK1, SK2, SK3, and SK4 (often referred to as intermediate conductance). The physiological roles of the SK channels have been especially studied in the nervous system, where for example they are key regulators of neuronal excitability and of neurotransmitter release, and in smooth muscle, where they are crucial in modulating the tone of vascular, broncho-tracheal, urethral, uterine or gastro-intestinal musculature.

Compound 1 is a small molecule modulator of potassium ion channels showing great therapeutic potential for treating a variety of diseases characterized by dysfunction of potassium ion channels and dysfunction from other causes which influence these potassium channels. Compound 1 is exemplified in U.S. Pat. No. 9,975,886, the contents of which are incorporated herein by reference, and has the structure:

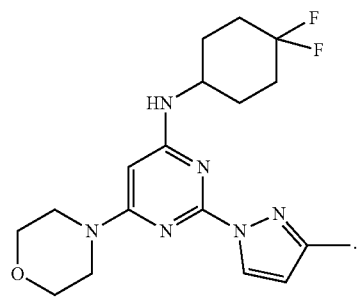 [SMILES: Cc1ccn(-c2nc(NC3CCC(F)(F)CC3)cc(N3CCOCC3)n2)n1]

The development of alternative forms of Compound 1 represents an attractive area to further the treatment of diseases such as those responsive to the modulation of the small conductance calcium-activated potassium subtype 2(SK2) channel.

SUMMARY

Provided herein are amorphous and crystalline forms of Compound 1.

Also provided herein are pharmaceutical compositions comprising one or more of the disclosed amorphous or crystalline forms of Compound 1.

Further provided is the use of one or more of the disclosed amorphous or crystalline forms of Compound 1 in the treatment diseases and/or disorders associated with the activity of potassium channels.

Processes for making the disclosed amorphous and crystalline forms are also provided.

DETAILED DESCRIPTION

1. Definitions

Figure 1:
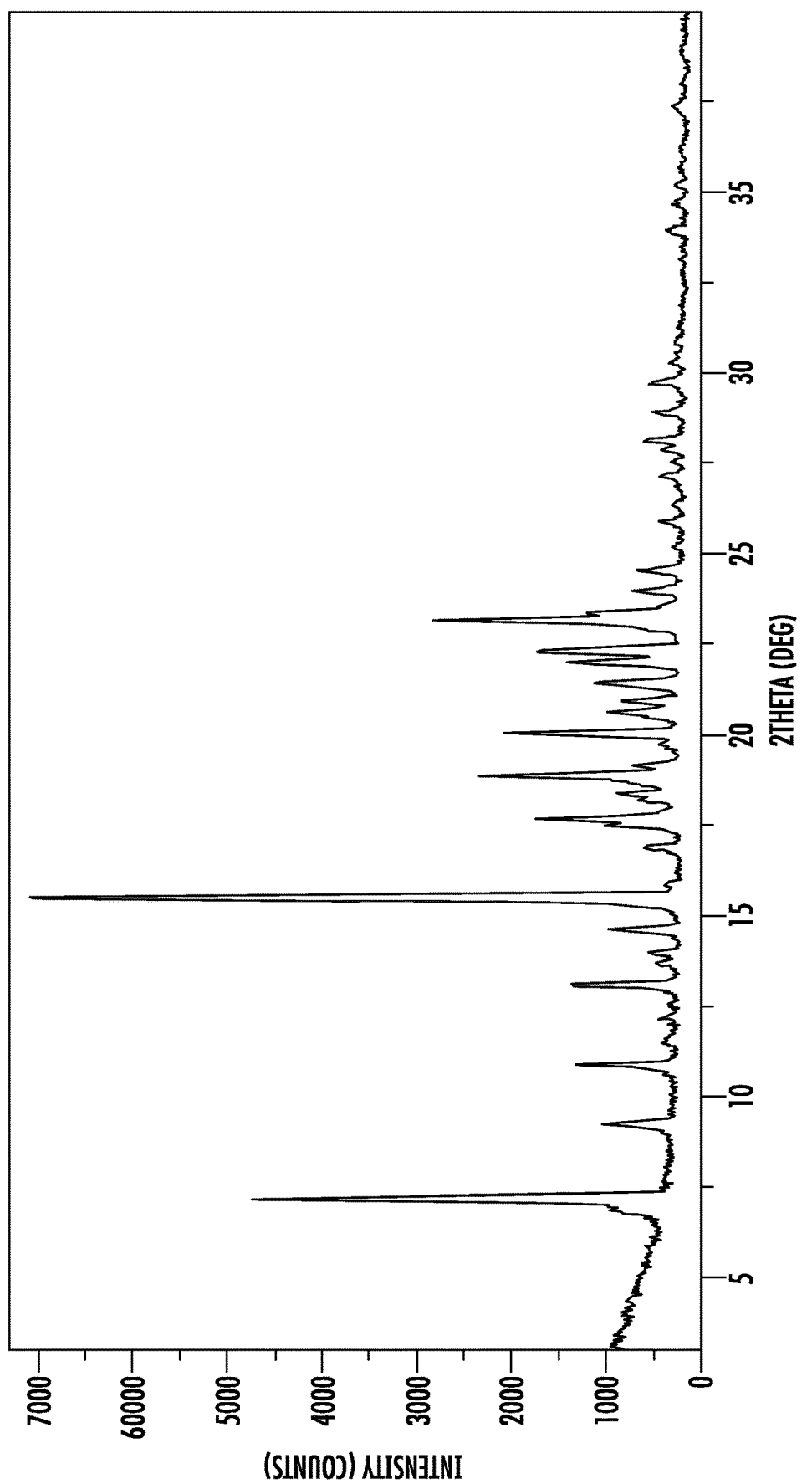
FIG. 1 depicts an x-ray powder diffraction (XRPD) pattern for crystalline Form B.

As used herein, "crystalline" refers to a solid form of a compound wherein there exists long-range atomic order in the positions of the atoms. The crystalline nature of a solid can be confirmed, for example, by examination of the X-ray powder diffraction pattern.

As used herein, a "single crystalline form" means that the recited compound, i.e., Compound 1, is present as a single crystal or a plurality of crystals in which each crystal has the same crystal form (e.g., Form B, C, D, E, or F). When the crystal form is defined as a specified percentage of one particular single crystalline form of the compound, the remainder is made up of amorphous form and/or crystalline forms other than the one or more particular forms that are specified. In one embodiment, e.g., a disclosed crystalline form is at least 60% a single crystalline form, at least 70% a single crystalline form, at least 75% a single crystalline form, at least 80% a single crystalline form, least 85% a single crystalline form, at least 90% a single crystalline form, at least 95% a single crystalline form, at least 96% a single crystalline form, at least 97% a single crystalline form, at least 98% a single crystalline form, or at least 99% a single crystalline form by weight. Percent by weight of a particular crystal form is determined by the weight of the particular crystal form divided by the sum weight of the particular crystal, plus the weight of the other crystal forms present plus the weight of amorphous form present multiplied by 100%.

Unless otherwise specified, Form B, Form C, Form D, and Form F are each single crystalline forms as defined herein. Therefore, "Form B", "single crystalline Form B", "single crystalline Form B", or "single solid" when referring to "Form B" are used interchangeably. The same applies for Form C, Form D, and Form F.

Chemical purity refers to extent by which the disclosed form is free from materials having different chemical structures. Chemical purity of the compound in the disclosed crystal forms means the weight of the compound divided by the sum of the weight of the compound plus materials/impurities having different chemical structures multiplied by 100%, i.e., percent by weight. In one embodiment, the compound in one or more of the disclosed crystalline forms has a chemical purity of at least 60%, at least 65%, at least 70%, at least 75%, at least 80%, at least 85%, at least 90%, at least 95%, at least 96%, at least 97%, at least 98%, or at least 99% by weight.

The term "amorphous" refers to a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

The term "anhydrous" and "anhydrate" are used interchangeably and mean that the referenced crystalline form has substantially no water in the crystal lattice, e.g., less than 0.1% by weight as determined by Karl Fisher analysis.

The term "solvate" refers to the physical association of a crystalline or amorphous form of Compound 1 as described herein with one or more solvent molecules. In certain instances, the solvate will be capable of isolation, for example when one or more solvent molecules are incorporated in the crystal lattice of a crystalline solid. Exemplary solvates include hydrates, isopropanolates, ethanolates, methanolates, dichloromethanolates, and the like.

Compound 1 refers to a compound having the following structural formula:

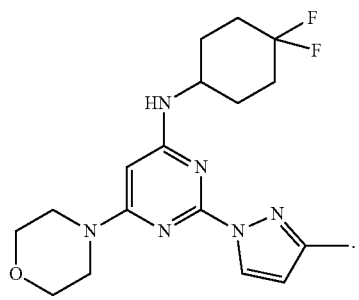 [SMILES: Cc1ccn(-c2nc(NC3CCC(F)(F)CC3)cc(N3CCOCC3)n2)n1]

The 2-theta values of the X-ray powder diffraction patterns for the crystalline forms described herein may vary slightly from one instrument to another and also depending on variations in sample preparation and batch to batch variation due to factors such as temperature variation, sample displacement, and the presence or absence of an internal standard. Therefore, unless otherwise defined, the XRPD patterns/assignments recited herein are not to be construed as absolute and can vary ±0.2 degrees. It is well known in the art that this variability will account for the above factors without hindering the unequivocal identification of a crystal form. Unless otherwise specified, the 2-theta values provided herein were obtained using Cu Kα1 radiation.

Temperature values, e.g., for DSC peaks herein may vary slightly from one instrument to another and also depending on variations in sample preparation, batch to batch variation, and environmental factors. Therefore, unless otherwise defined, temperature values recited herein are not to be construed as absolute and can vary ±5 degrees or ±2 degrees.

"Substantially the same XRPD pattern" or "an X-ray powder diffraction pattern substantially similar to" a defined figure means that for comparison purposes, at least 90% of the peaks shown are present. It is to be further understood that for comparison purposes some variability in peak intensities from those shown are allowed, such as ±0.2 degrees.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "pharmaceutically acceptable carrier" refers to a non-toxic carrier, adjuvant, or vehicle that does not destroy the pharmacological activity of the compound with which it is formulated. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject.

2. Exemplary Forms

Provided herein is a crystalline Form B of a compound having the structural formula:

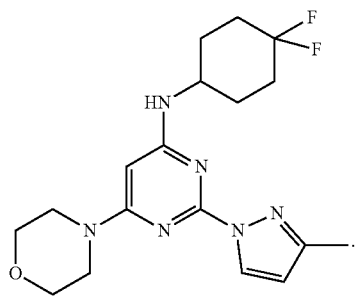 [SMILES: Cc1ccn(-c2nc(NC3CCC(F)(F)CC3)cc(N3CCOCC3)n2)n1]

In one aspect, crystalline Form B is characterized by at least three x-ray powder diffraction peaks at 2Θ angles selected from 7.2°, 15.5°, 17.7°, 18.9°, 20.1°, 22.3°, and 23.2°. In other aspects, crystalline Form B is characterized by at least four x-ray powder diffraction peaks at 2Θ angles selected from 7.2°, 15.5°, 17.7°, 18.9°, 20.1°, 22.3°, and 23.2°. In other aspects, crystalline Form B is characterized by at least five x-ray powder diffraction peaks at 2Θ angles selected from 7.2°, 15.5°, 17.7°, 18.9°, 20.1°, 22.3°, and 23.2°. In other aspects, crystalline Form B is characterized by at least six x-ray powder diffraction peaks at 2Θ angles selected from 7.2°, 15.5°, 17.7°, 18.9°, 20.1°, 22.3°, and 23.2°. In other aspects, crystalline Form B is characterized by x-ray powder diffraction peaks at 2Θ angles selected from 7.2°, 15.5°, 17.7°, 18.9°, 20.1°, 22.3°, and 23.2°. In other aspects, crystalline Form B is characterized by x-ray powder diffraction peaks at 2Θ angles selected from 7.2°, 15.5°, and 23.2°. In other aspects, crystalline Form B is characterized by x-ray powder diffraction peaks at 2Θ angles selected from 7.2°, 15.5°, 18.9°, and 23.2°. In other aspects, crystalline Form B is characterized by x-ray powder diffraction peaks at 2Θ angles selected from 7.2°, 15.5°, 18.9°, 20.1°, and 23.2°. In other aspects, crystalline Form B is characterized by x-ray powder diffraction peaks at 2Θ angles selected from 7.2°, 9.2°, 10.9°, 13.1°, 14.6°, 15.5°, 17.7°, 18.9°, 20.1°, 20.6°, 21.4°, 22.0°, 22.3°, and 23.2°. In other aspects, crystalline Form B is characterized by x-ray powder diffraction peaks at 2Θ angles selected from 7.2°, 9.2°, 10.9°, 11.5°, 12.2°, 13.1°, 13.7°, 14.0°, 14.6°, 15.5°, 16.9°, 17.7°, 18.4°, 18.9°, 19.1°, 20.1°, 20.6°, 20.9°, 21.4°, 22.0°, 22.3°, 23.2°, 24.0°, 24.5°, 25.2°, 25.9°, 26.4°, 27.1°, 28.1°, 28.9°, 29.7°, 33.9°, 34.7°, 35.2°, 37.3°, and 38.9°. In other aspects, crystalline Form B is characterized by at least four, at least five, at least six, at least seven, at least eight, at least nine, or at least ten, at least eleven, at least twelve, at least thirteen, at least fourteen, at least fifteen, at least sixteen, at least seventeen, at least eighteen, at least nineteen, or at least twenty x-ray powder diffraction peaks at 2Θ angles selected from those in Table 16. In other aspects, crystalline Form B is characterized by an XRPD (x-ray powder diffraction) substantially similar to FIG. 1. In other aspects, crystalline Form B is characterized by a Thermogravimetric analysis (TGA) of a 0.1% weight loss up to 150° C. or Differential Scanning calorimetry (DSC) of a sharp endotherm at 170.6° C. (onset temperature), or both, wherein the crystalline Form B may also comprise XRPD peaks at 2Θ angles selected from those above. In other aspects, crystalline Form B is characterized by a Thermogravimetric analysis (TGA) or Differential Scanning calorimetry (DSC) substantially similar to FIG. 2, wherein the crystalline Form B may also comprise XRPD peaks at 2Θ angles selected from those above. In other aspects, crystalline Form B crystallizes in the P2$_1$/c monoclinic space group, wherein the crystalline Form B may also comprise XRPD peaks at 2Θ angles selected from those above and/or the TGA or DSC values or figures recited above. In other aspects, crystalline Form B is anhydrous, wherein the crystalline Form B may also comprise XRPD peaks at 2Θ angles selected from those above, the TGA or DSC values or figures recited above, and/or crystallize in the P2$_1$/c monoclinic space group.

Also provided herein is a crystalline Form C of a compound having the structural formula:

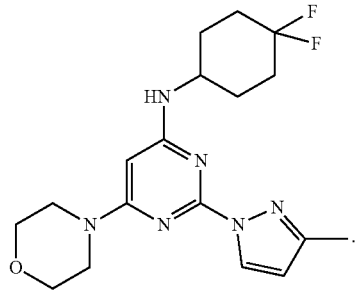

Figure 4:
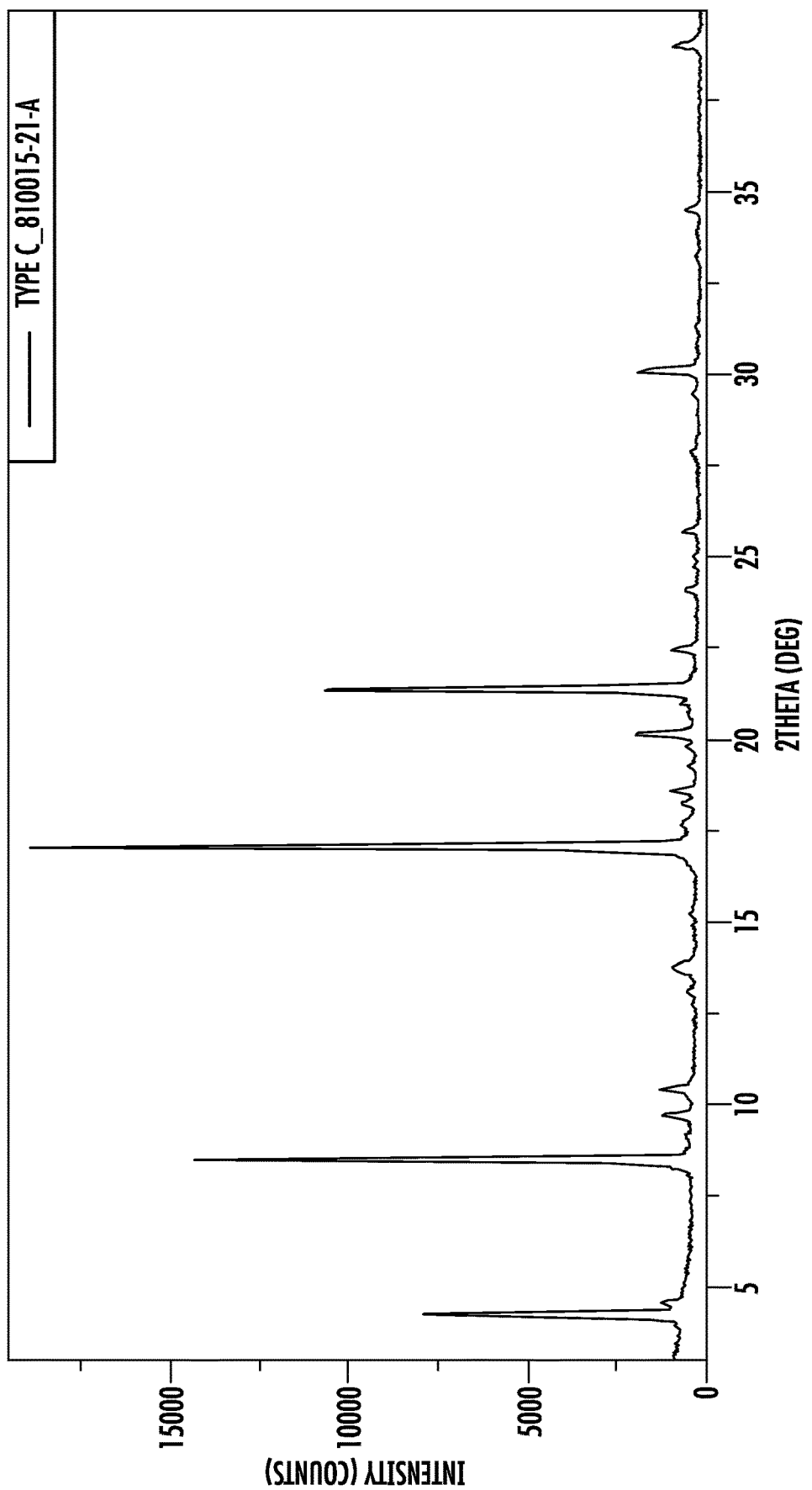
FIG. 4 depicts an x-ray powder diffraction (XRPD) pattern for crystalline Form C.

In one aspect, crystalline Form C is characterized by at least three x-ray powder diffraction peaks at 2Θ angles selected from 4.2°, 8.5°, 17.0°, 20.2°, and 21.4°. In other aspects, crystalline Form C is characterized by at least four x-ray powder diffraction peaks at 2Θ angles selected from 4.2°, 8.5°, 17.0°, 20.2°, and 21.4°. In other aspects, crystalline Form C is characterized by x-ray powder diffraction peaks at 2Θ angles selected from 4.2°, 8.5°, 17.0°, 20.2°, and 21.4°. In other aspects, crystalline Form C is characterized by x-ray powder diffraction peaks at 2Θ angles selected from 4.2°, 4.5°, 8.5°, 9.1°, 9.7°, 10.4°, 13.1°, 13.7°, 15.2°, 17.0°, 17.7°, 18.2°, 18.6°, 19.3°, 19.8°, 20.2°, 21.4°, 22.5°, and 24.1°. In other aspects, crystal Form C is characterized by an XRPD substantially similar to FIG. 4. In other aspects, crystalline Form C is characterized by a Thermogravimetric analysis (TGA) curve with a step weight loss of 6.6% up to 150° C., or a Differential Scanning calorimetry (DSC) curve with three endotherms at 74.9° C. and 168.8° C. (onset temperatures) and 93.3° C. (peak temperature), or both, wherein the crystalline Form C may also comprise XRPD peaks at 2Θ angles selected from those above. In other aspects, crystalline Form C is characterized by a Thermogravimetric analysis (TGA) or Differential Scanning calorimetry (DSC) substantially similar to FIG. 5, wherein the crystalline Form C may also comprise XRPD peaks at 2Θ angles selected from those above.

Also provided herein is a crystalline Form D of a compound having the structural formula:

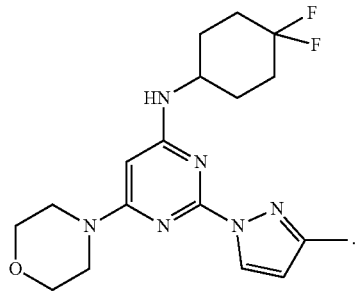

Figure 6:
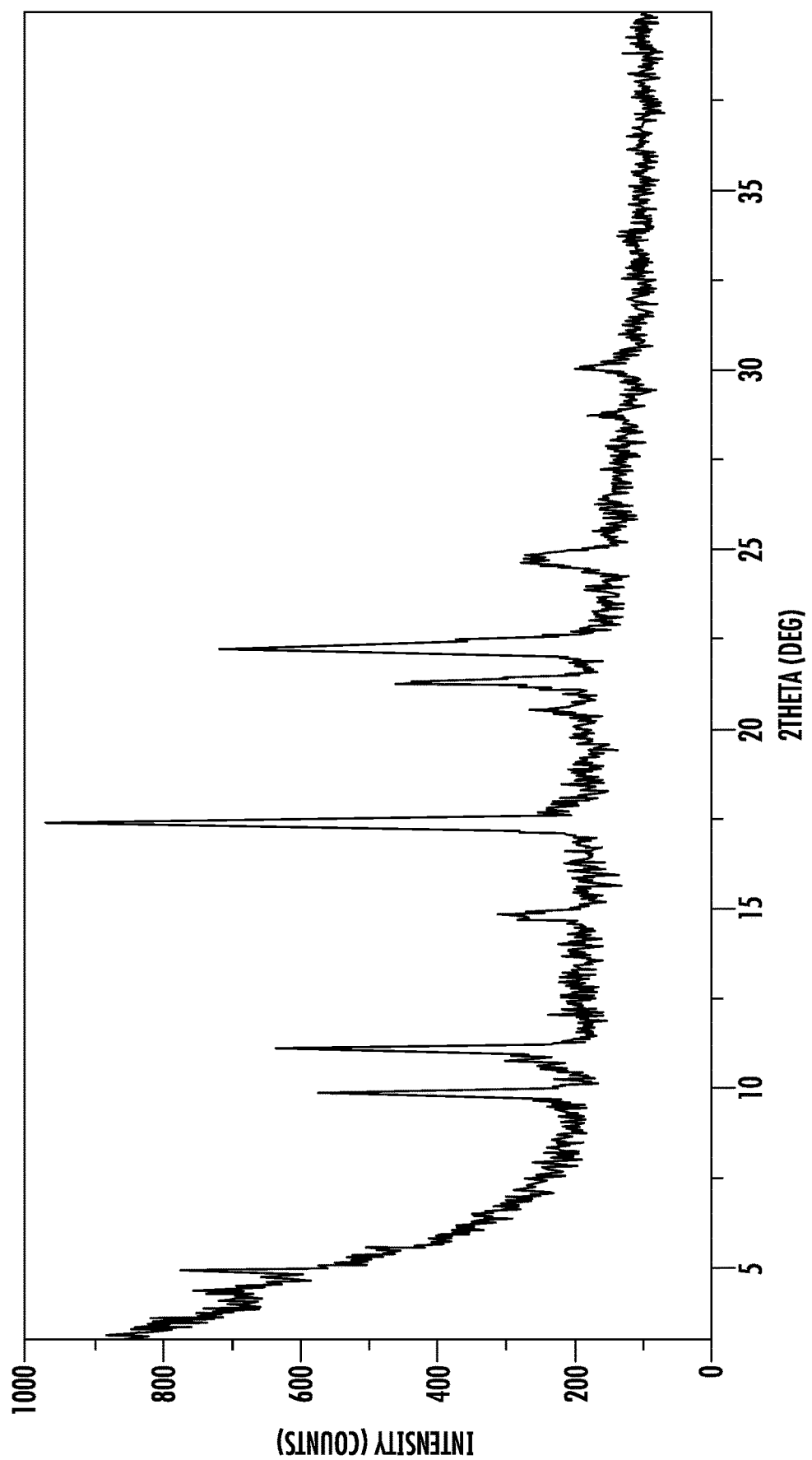
FIG. 6 depicts an x-ray powder diffraction (XRPD) pattern for crystalline Form D.
Figure 7:
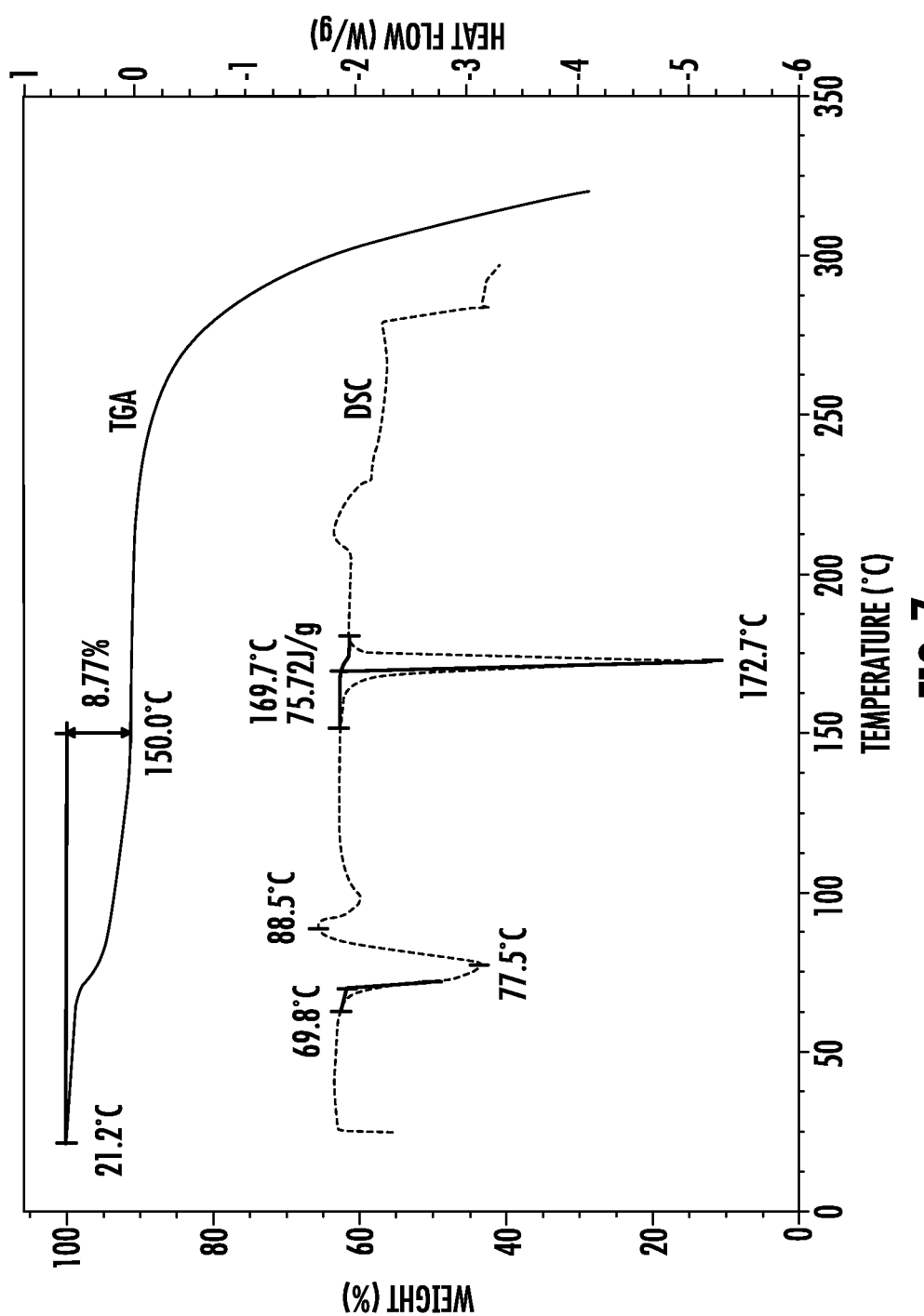
FIG. 7 depicts the combined thermogravimetric analysis (TGA) thermogram and differential scanning calorimetry (DSC) thermogram for crystalline Form D.

In one aspect, crystalline Form D is characterized by at least three x-ray powder diffraction peaks at 2Θ angles selected from 4.9°, 9.9°, 11.1°, 17.4°, 21.3°, 22.2°, and 24.8°. In other aspects, crystalline Form D is characterized by at least four x-ray powder diffraction peaks at 2Θ angles selected from 4.9°, 9.9°, 11.1°, 17.4°, 21.3°, 22.2°, and 24.8°. In other aspects, crystalline Form D is characterized by at least five x-ray powder diffraction peaks at 2Θ angles selected from 4.9°, 9.9°, 11.1°, 17.4°, 21.3°, 22.2°, and 24.8°. In other aspects, crystalline Form D is characterized by at least six x-ray powder diffraction peaks at 2Θ angles selected from 4.9°, 9.9°, 11.1°, 17.4°, 21.3°, 22.2°, and 24.8°. In other aspects, crystalline Form D is characterized by x-ray powder diffraction peaks at 2Θ angles selected from 4.9°, 9.9°, 11.1°, 17.4°, 21.3°, 22.2°, and 24.8°. In other aspects, crystalline Form D is characterized by x-ray powder diffraction peaks at 2Θ angles selected from 4.9°, 9.9°, 11.1°, 14.8°, 17.4°, 21.3°, 22.2°, 24.8°, and 30.1°. In other aspects, crystal Form D is characterized by an XRPD substantially similar to FIG. 6. In other aspects, crystalline Form D is characterized by a Thermogravimetric analysis (TGA) curve with a step weight loss of 8.8% up to 150° C., or a Differential Scanning calorimetry (DSC) curve with two endotherms at 69.8° C. and 169.7° C. (onset temperatures) and an exotherm at 88.5° C. (peak temperature), or both, wherein the crystalline Form D may also comprise XRPD peaks at 2Θ angles selected from those above. In other aspects, crystalline Form D is characterized by a Thermogravimetric analysis (TGA) or Differential Scanning calorimetry (DSC) substantially similar to FIG. 7, wherein the crystalline Form D may also comprise XRPD peaks at 2Θ angles selected from those above.

Also provided herein is a crystalline Form E of a compound having the structural formula:

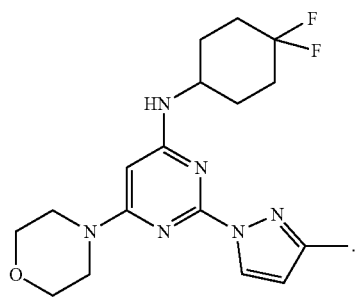

In one aspect, crystalline Form E is characterized by at least three x-ray powder diffraction peaks at 2Θ angles selected from 8.0°, 16.0°, 16.8°, 17.1°, 18.8°, 19.3°, and 23.4°. In other aspects, crystalline Form E is characterized by at least four x-ray powder diffraction peaks at 2Θ angles selected from 8.0°, 16.0°, 16.8°, 17.1°, 18.8°, 19.3°, and 23.4°. In other aspects, crystalline Form E is characterized by at least five x-ray powder diffraction peaks at 2Θ angles selected from 8.0°, 16.0°, 16.8°, 17.1°, 18.8°, 19.3°, and 23.4°. In other aspects, crystalline Form E is characterized by at least six x-ray powder diffraction peaks at 2Θ angles selected from 8.0°, 16.0°, 16.8°, 17.1°, 18.8°, 19.3°, and 23.4°. In other aspects, crystalline Form E is characterized by x-ray powder diffraction peaks at 2Θ angles selected from 8.0°, 16.0°, 16.8°, 17.1°, 18.8°, 19.3°, and 23.4°. In other aspects, crystalline Form E is characterized by x-ray powder diffraction peaks at 2Θ angles selected from 3.2°, 8.0°, 9.6°, 11.0°, 12.1°, 12.6°, 14.1°, 14.7°, 16.0°, 16.8°, 17.1°, 17.7°, 18.8°, 19.3°, 19.6°, 20.1°, 21.5°, 21.7°, 22.2°, 22.4°, 23.4°, 24.3°, 25.5°, 26.9°, 27.8°, 28.3°, 29.3°, and 31.4°. In other aspects, crystalline Form E is characterized by an XRPD substantially similar to FIG. 8. In other aspects, crystalline Form E is characterized by a Thermogravimetric analysis (TGA) curve with a step weight loss of 8.1% up to 110° C., or a Differential Scanning calorimetry (DSC) curve two endotherms at 91.0° C. and 170.5° C. (onset temperatures), or both, wherein the crystalline Form E may also comprise XRPD peaks at 2Θ angles selected from those above. In other aspects, crystalline Form E is characterized by a Thermogravimetric analysis (TGA) or Differential Scanning calorimetry (DSC) substantially similar to FIG. 9, wherein the crystalline Form E may also comprise XRPD peaks at 2Θ angles selected from those above.

Also provided herein is a crystalline Form F of a compound having the structural formula:

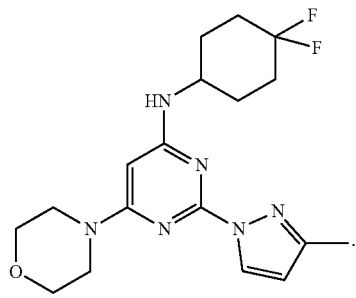 [SMILES: Cc1ccn(-c2nc(NC3CCC(F)(F)CC3)cc(N3CCOCC3)n2)n1]

Figure 10:
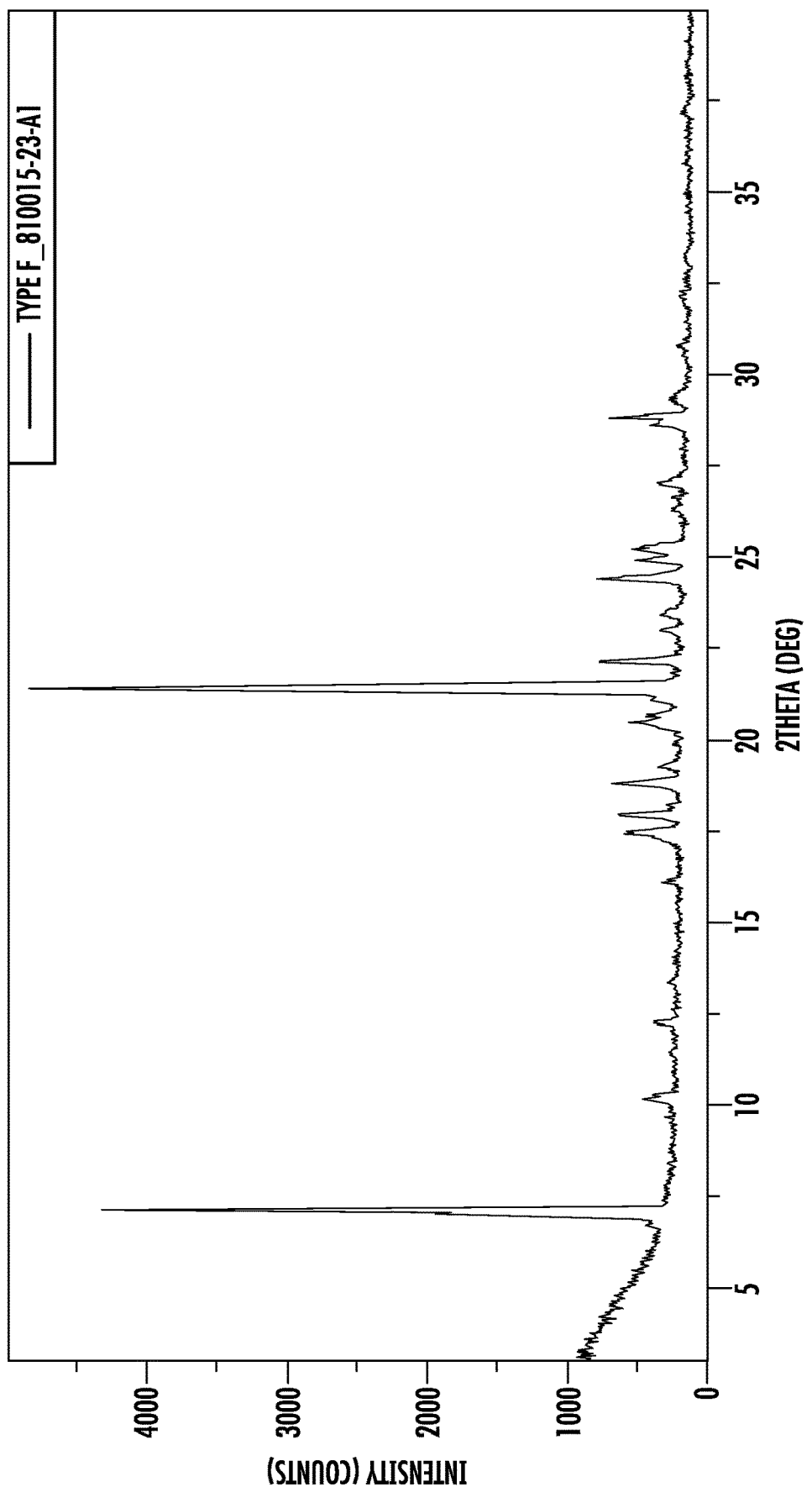
FIG. 10 depicts an x-ray powder diffraction (XRPD) pattern for crystalline Form F.

In one aspect, crystalline Form F is characterized by at least three x-ray powder diffraction peaks at 2Θ angles selected from 7.1°, 17.9°, 18.8°, 21.4°, 22.1°, 24.4°, and 28.8°. In other aspects, crystalline Form F is characterized by at least four x-ray powder diffraction peaks at 2Θ angles selected from 7.1°, 17.9°, 18.8°, 21.4°, 22.1°, 24.4°, and 28.8°. In other aspects, crystalline Form F is characterized by at least five x-ray powder diffraction peaks at 2Θ angles selected from 7.1°, 17.9°, 18.8°, 21.4°, 22.1°, 24.4°, and 28.8°. In other aspects, crystalline Form F is characterized by at least six x-ray powder diffraction peaks at 2Θ angles selected from 7.1°, 17.9°, 18.8°, 21.4°, 22.1°, 24.4°, and 28.8°. In other aspects, crystalline Form F is characterized by x-ray powder diffraction peaks at 2Θ angles selected from 7.1°, 17.9°, 18.8°, 21.4°, 22.1°, 24.4°, and 28.8°. In other aspects, crystalline Form F is characterized by x-ray powder diffraction peaks at 2Θ angles selected from 3.4°, 7.1°, 10.2°, 12.2°, 16.1°, 17.5°, 17.9°, 18.8°, 19.3°, 20.5°, 21.4°, 22.2°, 23.0°, 23.4°, 24.4°, 24.9°, 25.2°, 27.0°, 28.8°, 29.3°, 30.7°, and 32.1°. In other aspects, crystalline Form F is characterized by an XRPD substantially similar to FIG. 10. In other aspects, crystalline Form F is characterized by a Thermogravimetric analysis (TGA) curve with a step weight loss of 18.1% up to 150° C., or a Differential Scanning calorimetry (DSC) curve with two endotherms at 75.7° C. and 168.3° C. (onset temperatures) and an exotherm at 86.9° C. (peak temperature), or both, wherein the crystalline Form F may also comprise XRPD peaks at 2Θ angles selected from those above. In other aspects, crystalline Form F is characterized by a Thermogravimetric analysis (TGA) or Differential Scanning calorimetry (DSC) substantially similar to FIG. 11, wherein the crystalline Form F may also comprise XRPD peaks at 2Θ angles selected from those above.

Also provided herein is an amorphous form of a compound having the structural formula:

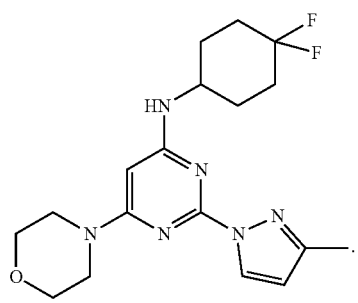 [SMILES: Cc1ccn(-c2nc(NC3CCC(F)(F)CC3)cc(N3CCOCC3)n2)n1]

3. Uses, Formulation and Administration

The crystalline and amorphous forms described herein and compositions thereof are useful in treating diseases and/or disorders associated with the activity of potassium channels. Such diseases and/or disorders include e.g., neurodegenerative and neurological conditions (e.g., Parkinson's disease, tremors, Alzheimer's disease, dementia, amyotrophic lateral sclerosis (ALS) ataxia, anxiety, depression, mood disorders, memory and attention deficits, bipolar disorder, psychosis, schizophrenia, traumatic brain injury, and narcolepsy), heart disease and related conditions (e.g., ischaemic heart disease, coronary heart disease, angina pectoris, and coronary artery spasms), metabolic disease and bladder diseases (e.g., bladder spasms, urinary incontinence, bladder outflow obstruction, gastrointestinal dysfunction, irritable bowel syndrome, and diabetes), withdrawal symptoms associated with termination of addiction, and other conditions associated with the modulation of potassium channels such as e.g., respiratory diseases, epilepsy, convulsions, seizures, absence seizures, vascular spasms, renal disorders (e.g., polycystic kidney disease), erectile dysfunction, secretory diarrhoea, ischaemia, cerebral ischaemia, dysmenorrhea, Reynaud's disease, intermittent claudication, Sjorgren's syndrome, arrhythmia, hypertension, myotonic muscle dystrophia, spasticity, xerostomi, hyperinsulinemia, premature labor, baldness, cancer, immune suppression, migraine and pain.

The present disclosure also provides a method of modulating the activity of a potassium channel in a subject comprising the step of administering a crystalline or amorphous form or composition described herein. In another aspect, the present disclosure provides a method of positively modulating a SK2 channel in a cell comprising the step of contacting the cell with a crystalline or amorphous form or composition described herein.

In one aspect, the provided crystalline and amorphous forms described herein and compositions thereof are used to treat tremors. Tremors include, but are not limited to rest, active, postural, kinetic, intention, task specific, and idiopathic tremors. In one aspect, the provided crystalline and amorphous forms described herein and compositions thereof are used to treat postural and active tremors. Examples of postural and/or active tremors include essential tremor, drug-induced parkinsonism, neuropathic tremor, and tremors induced from toxins (e.g., alcohol withdrawal or from exposure to heavy metals). In one aspect, the provided crystalline and amorphous forms described herein and compositions thereof are used to treat essential tremor.

The present disclosure further provides a method of treating essential tremor in a subject comprising the step of administering a crystalline or amorphous form or composition described herein.

In some aspects, the crystalline and amorphous forms described herein and compositions thereof are useful in treating a disease or condition selected from a neurodegenerative disease, dementia, heart disease, withdrawal symptoms associated with termination of addiction, metabolic disease, and bladder disease. In some aspects, the crystalline and amorphous forms described herein and compositions thereof are useful in treating a disease or condition selected from ataxia, dystonia, Parkinson's disease, ischemia, traumatic brain injury, amyotrophic lateral sclerosis, hypertension, atherosclerosis, diabetes, arrhythmia, over-active bladder, and withdrawal symptoms caused by the termination of abuse of alcohol and other drugs of abuse. In some aspects, the crystalline and amorphous forms described herein and compositions thereof are useful in treating ataxia. In some aspects, the crystalline and amorphous forms described herein and compositions thereof are useful in treating spinocerebellar ataxia.

Also provided are pharmaceutically acceptable compositions comprising one or more of the disclosed crystalline or amorphous forms described herein; and a pharmaceutically acceptable carrier. These compositions can be used to treat one or more of the diseases and conditions described above.

Use of a disclosed crystalline or amorphous form described herein in the manufacture of a medicament for treating a disease or condition recited herein is also provided.

A crystalline or amorphous form described herein for use in treating a disease or condition recited herein is also provided.

Compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a crystalline or amorphous form are included herein.

The amount of provided crystalline or amorphous forms that may be combined with carrier materials to produce a composition in a single dosage form will vary depending upon the patient to be treated and the particular mode of administration. In some embodiments, provided compositions may be formulated so that a dosage of between 0.01-100 mg/kg body weight/day of the provided compound, such as e.g., 0.1-100 mg/kg body weight/day, can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided crystalline and amorphous form in the composition will also depend upon the particular crystalline and amorphous form in the composition.

EXEMPLIFICATION

As depicted in the Examples below, crystalline and amorphous forms are prepared according to the following general procedures.

Abbreviations

| Abbreviation | Solvent |
|---|---|
| MeOH | Methanol |
| EtOH | Ethanol |
| IPA | Isopropyl alcohol |
| MIBK | 4-Methyl-2-pentanone |
| EtOAc | Ethyl acetate |
| IPAc | Isopropyl acetate |
| MTBE | Methyl tert-butyl ether |
| THF | Tetrahydrofuran |
| 2-MeTHF | 2-Methyltetrahydrofuran |
| DCM | Dichloromethane |
| ACN | Acetonitrile |
| DMSO | Dimethylsulfoxide |
| DMAc | N,N-Dimethylacetamide |
| NMP | 1-Methyl-2-pyrrolidone |

Units

| Full Name | Abbreviation |
|---|---|
| Celsius | C. |
| Degrees | ° |
| Equivalents | eq. |
| Gram | g |
| Hour | hr |
| Kelvin | K |
| Liters | L |
| Milligrams | mg |
| Milliliters | mL |
| Minute | min |
| Resolutions Per Minute | rpm |
| Room temperature | RT |
| Second | sec |
| volume | vol. |
| Volume ratio | v/v |

Units -continued

| Full Name | Abbreviation |
|---|---|
| Watt | W |
| Weight | wt. |
| Weight Percentage | wt. % |

1. Analytical Techniques

X-Ray Powder Diffraction (XRPD)

For XRPD analysis, a PANalytical Empyrean X-ray powder diffract meter was used. The XRPD parameters used are listed in Table 1.

TABLE 1

| Parameters | Empyrean | X' Pert3 |
|---|---|---|
| X-Ray wavelength | Cu, kα; Kα1 (Å): 1.540598 Kα2 (Å): 1.544426 intensity ratio Kα2/Kα1: 0.50 | Cu, kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA |
| Divergence slit | Automatic | Automatic |
| Scan mode | Continuous | Continuous |
| Scan range (°2TH) | 3°~40° | 3°~40° |
| Step size (°2TH) | 0.0167 | 0.0263 |
| Scan step time (s) | 18 | 50 |
| Test time (s) | 5 min 30 s | 5 min 04 s |

Thermogravimetric Analysis (TGA) and Differential Scanning Calorimetry (DSC)

TGA data were collected using a TA Q500/Q5000 TGA from TA Instruments. DSC was performed using a TA Q200/Q2000 DSC from TA Instruments. Detailed parameters used are listed in Table 2.

TABLE 2

| Parameters | TGA | DSC |
|---|---|---|
| Method | Ramp | Ramp |
| Sample pan | Aluminum, open | Aluminum, crimped |
| Temperature | RT-desired temperature | 25° C.-desired temperature |
| Heating rate | 10° C./min | 10° C./min |
| Purge gas | $N_2$ | $N_2$ |

Dynamic Vapor Sorption (DVS)

DVS was measured via a SMS (Surface Measurement Systems) DVS Intrinsic. The relative humidity at 25° C. were calibrated against deliquescence point of LiCl, $Mg(NO_3)_2$ and KCl. Parameters for DVS test were listed in Table 3.

TABLE 3

| Parameters | DVS |
|---|---|
| Temperature | 25° C. |
| Sample size | 10~20 mg |
| Gas and flow rate | $N_2$, 200 mL/min |
| dm/dt | 0.002%/min |
| MM. dm/dtstabilityduration | 10 min |

TABLE 3-continued

| Parameters | DVS |
|---|---|
| Max. equilibrium time | 180 min |
| RH range | 0% RH to 95% RH |
| RH step size | 10% RH from 0% RH to 90% RH |
| | 5% RH from 90% RH to 95% RH |

¹HNMR

¹HNMR was collected on Bruker 400M NMR Spectrometer using DMSO-d6.

Single Crystal X-Ray Diffraction (SCXRD)

The SCXRD data were collected at 150 K using Agilent SuperNova (Dual, Cu at zero, Eos) diffractometer (Cu/Kα radiation, λ=1.54178 Å). The parameters used are listed in Table 4. The microscopic picture was captured using Shanghai Cewei PXS9-T stereo microscope.

TABLE 4

| Device | Agilent SuperNova |
|---|---|
| X-Ray sources generator | SuperNova Microfocus X-ray Source (Cu/kα: 1.54178 Å) 50 KV, 0.8 mA |
| Detector | Eos CCD detector (Detector resolution: 16.0450 pixels mm$^{-1}$) |
| Goniometer | Four-circle Kappa geometry goniometer |
| Low Temperature Devices | Oxford Cryosystems |
| Software | CrysAlisPro (version: 1.171.38.41) |

Single Crystal Structure Determination

The structure was solved with the ShelXS structure solution program using Direct Methods (Sheldrick G M *Acta Cryst* 2008, A64:112-122) and refined with ShelXL refinement package using full-matrix least-squares on F contained in OLEX2 (Sheldrick G M *Acta Cryst* 2015, C71:3-8; Dolomanov O V, et al. *J Appl Cryst* 2006, 42:339-341). The calculated XRPD pattern was obtained by Mercury (Macrae C F, et al. *J Appl Cryst* 2006, 39:453-457) and the crystal structure representations were generated by Diamond (Brandenburg K *DIAMOND* 1999, Crystal Impact GbR, Bonn, Germany). The ORTEP (Oak Ridge Thermal Ellipsoid Plot) drawing was generated by ORTEP-III (Farrugia L J *J Appl Cryst* 2012, 45:849-854). The Platon program version: 21116 (Analysis of Potential Hydrogen Bonds with d(D . . . A)<R(D)+R(A)+0.50, d(H . . . A)<R(H)+R(A)−0.12 Angle, D-H . . . A>100.0 Degree) was used to calculate the classic hydrogen bonds in the crystal structure.

2. Polymorph Screening

Figure 12:
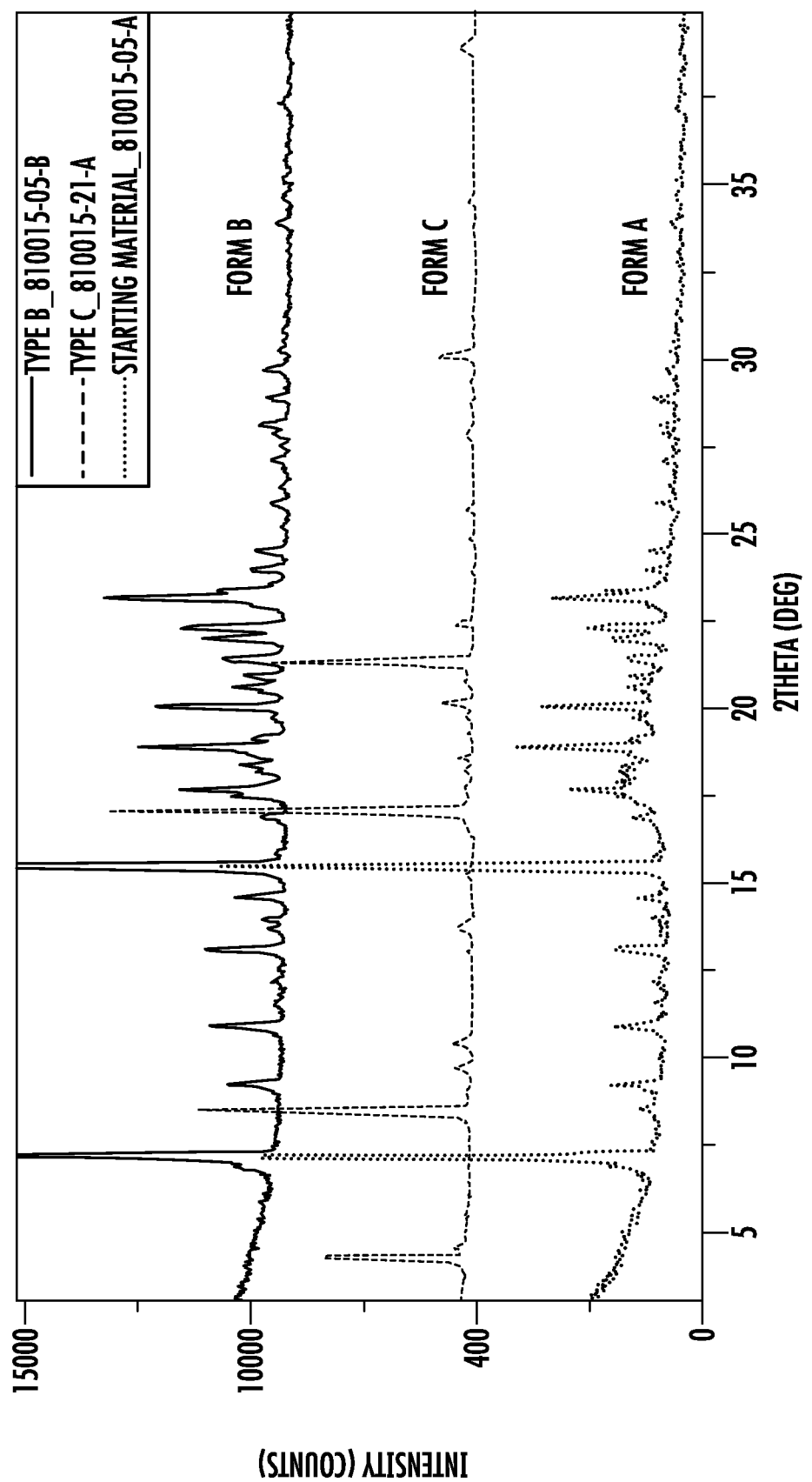
FIG. 12 depicts an x-ray powder diffraction (XRPD) pattern for crystalline Form A (a mixture of crystalline Form B and C).

The starting material for the following screens was obtained following the procedure set forth in Example 1 of U.S. Pat. No. 9,975,886, the entire contents of which are incorporated herein by reference, except that the material used for polymorph screening was isolated by trituration with alcoholic solvent instead of column chromatography. The XRPD of this material is shown in FIG. 12 as "Form A" and was determined to be a mixture of approximately 96% Form B and approximately 4% of one or more additional forms having certain characteristic peaks of Form C. These percentages are based on the relative intensity differences between the Form B representative peak at 7.2 and the Form C representative peak at 8.5 for the starting material (i.e., Form A) in FIG. 12. Estimating a baseline adjustment of about −1020 counts, the intensity for the Form B representative peak at 7.2 is about 8571 counts (about 9591-about 1020), whereas the intensity for the Form C representative peak at 8.5 is about 408 counts (about 1428-about 1020).

Solubility measurements for this mixture are provided in Table 5 and were obtained using the following procedure: approximately 2 mg of Form A was added into a 3-mL glass vial, a solvent of interest was then added into the vial until the solids were dissolved or a total volume of 1 mL was reached.

TABLE 5

| Solvent | Solubility (mg/mL) |
|---|---|
| MeOH | S > 44.0 |
| EtOH | S > 42.0 |
| IPA | 6.3 < S < 19.0 |
| acetone | S > 42.0 |
| MIBK | 20.0 < S < 40.0 |
| EtOAc | 21.0 < S < 42.0 |
| IPAc | 6.3 < S < 19.0 |
| MTBE | 2.0 < S < 6.7 |
| THF | S > 38.0 |
| 2-MeTHF | S > 40.0 |
| 1,4-dioxane | S > 42.0 |
| ACN | S > 40.0 |
| DCM | S > 40.0 |
| CHC13 | S > 44.0 |
| n-heptane | S < 2.1 |
| toluene | 6.7 < S < 20.0 |
| DMSO | S > 38.0 |
| DMAc | S > 40.0 |
| NMP | S > 42.0 |
| H$_2$O | S < 2.1 |

Using Form A as the starting material, preliminary polymorph screening experiments were performed. The methods used and identified crystalline forms are summarized in Table 6 and further detailed below. Form E was observed in-situ after either purging hydrate Form D sample under N$_2$ at 30° C. for 30 min or heating to 105° C.

TABLE 6

| Method | Single Crystal Forms Identified |
|---|---|
| Anti-solvent addition | Form B, |
| Solid vapor diffusion | Form B, Form E, amorphous Form |
| Slow evaporation | Form B, |
| Slow cooling | Form B, Form C |
| Slurry at RT | Form B |
| Slurry at 50° C. | Form B |
| Liquid vapor diffusion | Form B, Form C |
| Polymer induced crystallization | Form B, Form D |

Anti-Solvent Addition

A total of 14 anti-solvent addition experiments were carried out, using the solvent and anti-solvent systems listed in Table 7. About 20 mg of Form A was dissolved in 0.2~2.0 mL solvent to obtain a clear solution; the clear solution was magnetically stirred, followed by the step-wise addition of 0.1 mL anti-solvent until a precipitate appeared or the total amount of the anti-solvent reached 10.0 mL. The precipitate was then isolated for XRPD analysis.

TABLE 7

| Solvent | Anti-solvent | Single Solid Form |
|---|---|---|
| EtOH | n-heptane | Form B* |
| MIBK | | Form B |
| IPAc | | Form B |
| 2-MeTHF | | Form B |
| 1,4-dioxane | | Form B |
| DCM | | Form B |
| toluene | | Form B |
| MeOH | $H_2O$ | Form B |
| acetone | | Form B |
| 1,4-dioxane | | Form B |
| ACN | | Form B |
| DMSO | | Form B |
| NMP | | Form B |

*clear solution was obtained and then transferred to slurry at 5° C.

Solid Vapor Diffusion

Solid vapor diffusion experiments were conducted under 12 solvent conditions, as shown in Table 8. For each solvent condition, about 15 mg of Form A was weighed into a 3-mL vial, which was placed into a 20-mL vial with 4 mL volatile solvent. The 20-mL vial was sealed with a cap and kept at RT for 8 days allowing the solvent vapor to interact with Form A. The solids obtained were then analyzed by XRPD.

TABLE 8

| Solvent | Single Solid Form |
|---|---|
| $H_2O$ | Form B |
| DCM | Amorphous Form* |
| EtOH | Form B |
| MeOH | Form E |
| ACN | Form B |
| acetone | Form B |
| DMSO | Form B |
| EtOAc | Form B* |
| 1,4-dioxane | Form B |
| IPA | Form B |

*solid dissolved completely and then transferred to evaporate at RT.

Slow Evaporation

Slow evaporation experiments were performed under 12 different solvent conditions, as shown in Table 9. About 20 mg of Form A was dissolved in 0.4~3.0 mL solvent in a 3-mL glass vial. If not dissolved completely, suspensions were filtered using a PTFE membrane (pore size of 0.45 µm) and the filtrates would be used instead for the follow-up steps. The visually clear solutions were subjected to evaporation at RT with vials sealed by Parafilm®. The solids yielded were then isolated for XRPD analysis.

TABLE 9

| Solvent (v/v) | Single Solid Form |
|---|---|
| MeOH | Form B |
| acetone | Form B |
| IPAc | Form B |
| THF | Form B |
| $CHCl_3$ | Form B |
| EtOAc/MTBE (1:1) | Form B |
| EtOH/2-MeTHF (1:1) | Form B |
| DCM/MIBK (1:1) | Form B |
| THF/n-heptane (1:1) | Form B |
| ACN/$H_2O$ (1:1) | Form B |

Slow Cooling

Slow cooling experiments were conducted under 10 different solvent conditions, as shown in Table 10. For each solvent condition, about 20 mg Form A was suspended in 0.5-1.0 mL solvent in a 3-mL glass vial at RT. The suspension was then heated to 50° C., equilibrated for about 2 hrs and filtered into a new vial using a PTFE membrane (pore size of 0.45 µm). The filtrate was slowly cooled down to 5° C. at a rate of 0.1° C./min. The solids were then obtained and kept isothermally at 5° C. before being isolated for XRPD analysis.

TABLE 10

| Solvent (v/v) | Single Solid Form |
|---|---|
| IPA | Form C |
| IPAc | Form B |
| MTBE | Form B |
| toluene | Form B |
| IPA/MTBE (1:1) | Form C |
| IPAc/toluene (1:1) | Form B |
| acetone/n-heptane (1:1) | Form B |
| ACN/$H_2O$ (1:1) | Form B |
| THF/n-heptane (1:2) | Form B |

Slurry at RT

Slurry conversion experiments were conducted at RT under 20 different solvent systems, as shown in Table 11. About 20 mg Form A was suspended in 0.3 mL solvent in a 1.5-mL glass vial. After the suspension was stirred magnetically for 4 days at RT, the remaining solids were isolated for XRPD analysis.

TABLE 11

| Solvent (v/v) | Single Solid Form |
|---|---|
| IPA | Form B |
| IPAc | Form B |
| MTBE | Form B |
| n-heptane | Form B |
| toluene | Form B |
| $H_2O$ | Form B |
| MeOH/$H_2O$ (1:9) | Form B |
| EtOAc/n-heptane (1:9) | Form B |
| THF/$H_2O$ (1:4) | Form B |
| DCM/n-heptane (1:9) | Form B |
| IPAc/MTBE (1:1) | Form B |
| IPA/toluene (1:1) | Form B |
| MIBK/n-heptane (1:9) | Form B |
| DMAc/$H_2O$ (1:4) | Form B |
| acetone/n-heptane (1:9) | Form B |
| 1,4-dioxane/n-heptane (1:9) | Form B |
| IPA/$H_2O$ ($a_w$~0.2, 98:2) | Form B |
| IPA/$H_2O$ ($a_w$~0.4, 96:4) | Form B |
| IPA/$H_2O$ ($a_w$~0.6, 92:8) | Form B |
| IPA/$H_2O$ ($a_w$~0.8, 85:15) | Form B |

Slurry at 50° C.

Slurry conversion experiments were conducted at 50° C. under 14 different solvent systems, as shown in Table 12. About 25 mg Form A was suspended in 0.3 mL solvent in a 1.5-mL glass vial. After the suspension was stirred for about 4 days at 50° C., the remaining solids were isolated for XRPD analysis.

TABLE 12

Summary of slurry conversion experiments at 50° C.

| Solvent (v/v) | Single Solid Form |
|---|---|
| IPA | Form B |
| IPAc | Form B |
| MTBE | Form B |
| n-heptane | Form B |
| toluene | Form B |
| H₂O | Form B |
| IPAc/toluene (1:1) | Form B |
| IPA/MTBE (1:1) | Form B |
| EtOH/H₂O (1:9) | Form B |
| MIBK/n-heptane (1:9) | Form B |
| toluene/n-heptane (1:1) | Form B |
| ACN/H₂O (1:9) | Form B |
| CHCl₃/n-heptane (1:9) | Form B |
| THF/H₂O (1:9) | Form B |

Liquid Vapor Diffusion 12 liquid vapor diffusion experiments were conducted, using the solvent and anti-solvent systems listed in Table 13. About 20 mg Form A was dissolved in 0.2~2.0 mL appropriate solvent to obtain a clear solution in a 3-mL vial. This solution was then placed into a 20-mL vial with 4 mL volatile solvents. The 20-mL vial was sealed with a cap and kept at RT allowing sufficient time for organic vapor to interact with the solution. After the slow cooling process, clear solutions were obtained for the IPA and 2-MeTHF solvent systems, and solids were obtained for all other solvent systems. The solids were then isolated for XRPD analysis. The clear solutions were evaporated to dryness at RT to obtain the solids for XRPD analysis.

TABLE 13

| Solvent | Anti-solvent | Single Solid Form |
|---|---|---|
| IPA | n-heptane | Form C* |
| MIBK | | Form B |
| EtOAc | | Form B |
| MTBE | | Form B |
| CHCl₃ | | Form B |
| toluene | | Form B |
| EtOH | H₂O | Form B |
| acetone | | Form B |
| DMAc | | Form B |
| 1,4-dioxane | | Form B |
| ACN | | Form B |

*Clear solution was obtained and transferred to evaporate at RT.

Polymer Induced Crystallization

As shown in Table 14, polymer induced crystallization experiments were performed with two sets of polymer mixtures in six solvents, wherein polymer mixture A consists of polyvinyl pyrrolidone (PVP), polyvinyl alcohol (PVA), polyvinylchloride (PVC), polyvinyl acetate (PVAC), hypromellose (HPMC), methyl cellulose (MC) in a mass ratio of 1:1:1:1:1:1; and polymer mixture B consists of polycaprolactone (PCL), polyethylene glycol (PEG), poly (methyl methacrylate) (PMMA) sodium alginate (SA), and hydroxyethyl cellulose (HEC) in a mass ratio of 1:1:1:1:1. For each experiment, about 20 mg Form A was dissolved in 0.4~3.0 mL appropriate solvent to obtain a clear solution in a 3-mL vial. About 2 mg of a polymer mixture was added into 3-mL glass vial. All the samples were subjected to evaporate at RT to induce precipitation. The solids were isolated for XRPD analysis.

TABLE 14

| Solvent (v/v) | Polymer | Single Solid Form |
|---|---|---|
| EtOH | Polymer mixture A | Form D |
| MIBK/n-heptane (1:4) | | Form B |
| EtOAc/1,4-dioxane (1:1) | | Form B |
| CHCl₃ | Polymer mixture B | Form B |
| IPAc/ACN (1:1) | | Form B |
| 2-MeTHF/toluene (1:1) | | Form B |

Polymorph Screening Using the Amorphous Form as the Starting Material

The amorphous Form of Compound 1 was prepared according to the procedures set forth in Example 6 below. Using the amorphous Form as the starting material, 10 additional polymorph screening experiments, referred to as slurry conversion experiments, were conducted at RT or 50° C. in different solvent systems, as shown in Table 15. About 10 mg of the amorphous Form was suspended in 0.2~0.3 mL of solvent. After the suspension was stirred magnetically (~1000 rpm) at RT or 50° C., the remaining solids were isolated for XRPD analysis.

TABLE 15

| Solvent (v/v) | Temperature | Single Solid Form |
|---|---|---|
| H₂O | RT | Form B |
| n-heptane | | Form B |
| MTBE | | Form B |
| acetone/H₂O (1:9) | | Form B |
| CHCl₃/n-heptane (1:9) | | Form B |
| H₂O | 50° C. | Form B |
| n-heptane | | Form B |
| IPA/H₂O (1:4) | | Form B |
| EtOAc/n-heptane (1:9) | | Form B |
| MIBK/toluene (1:9) | | Form B |

3. Preparation of Various Forms

Example 1: Preparation of Single Crystalline Form B

Figure 2:
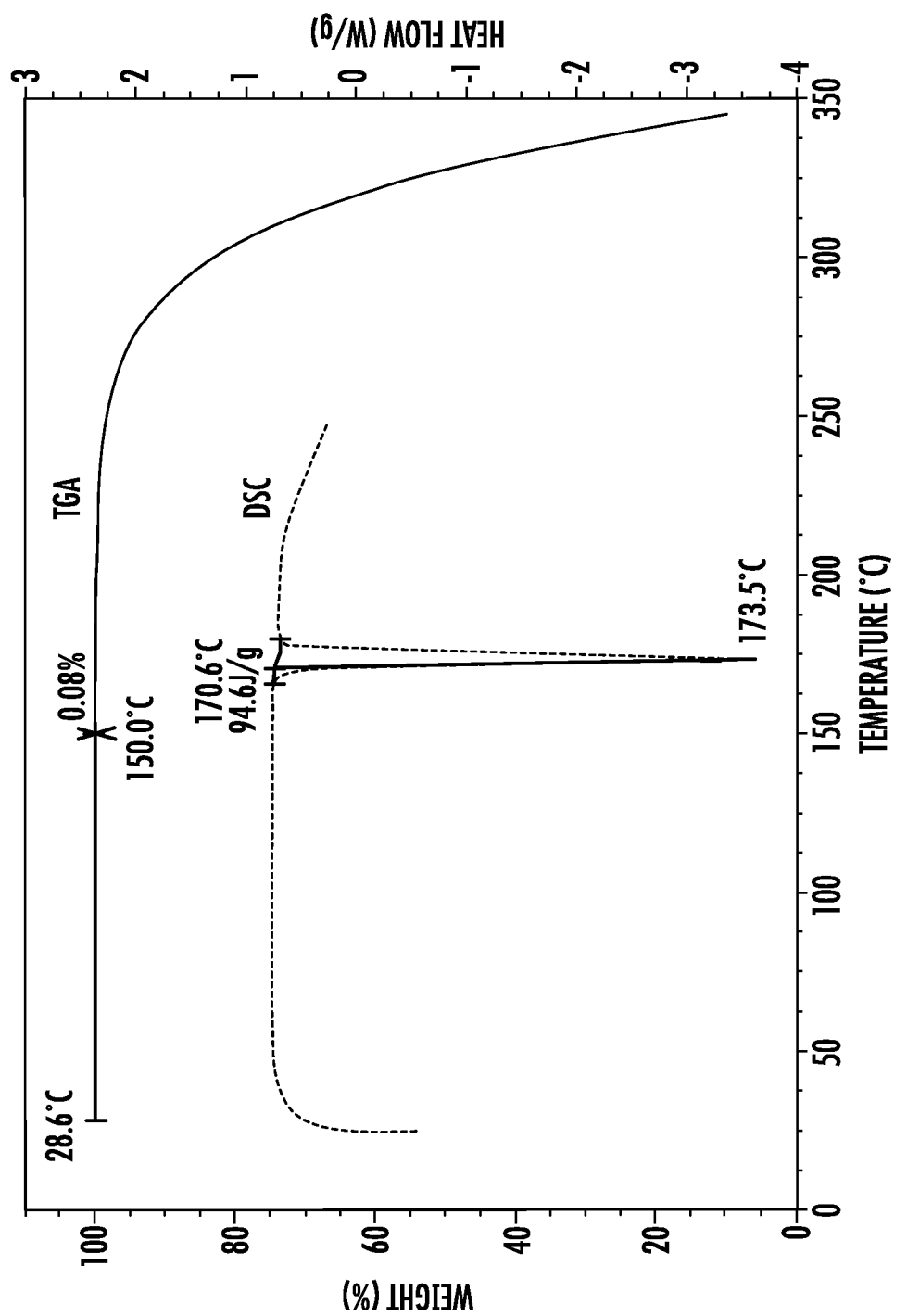
FIG. 2 depicts the combined thermogravimetric analysis (TGA) thermogram and differential scanning calorimetry (DSC) thermogram for crystalline Form B.

Form B was obtained via heating Form A to 140° C. and then cooled to RT. Form B showed a strong, unique XRPD pattern with sharp peaks and a flat baseline, indicative of a crystalline material (see FIG. 1 and Table 16). Form B showed a TGA curve with a 0.1% weight loss up to 150° C. and a DSC curve with a sharp endotherm at 170.6° C. (onset temperature) (FIG. 2). The low TGA weight loss and the sole sharp DSC endotherm suggested that Form B was an anhydrate.

Figure 3A:
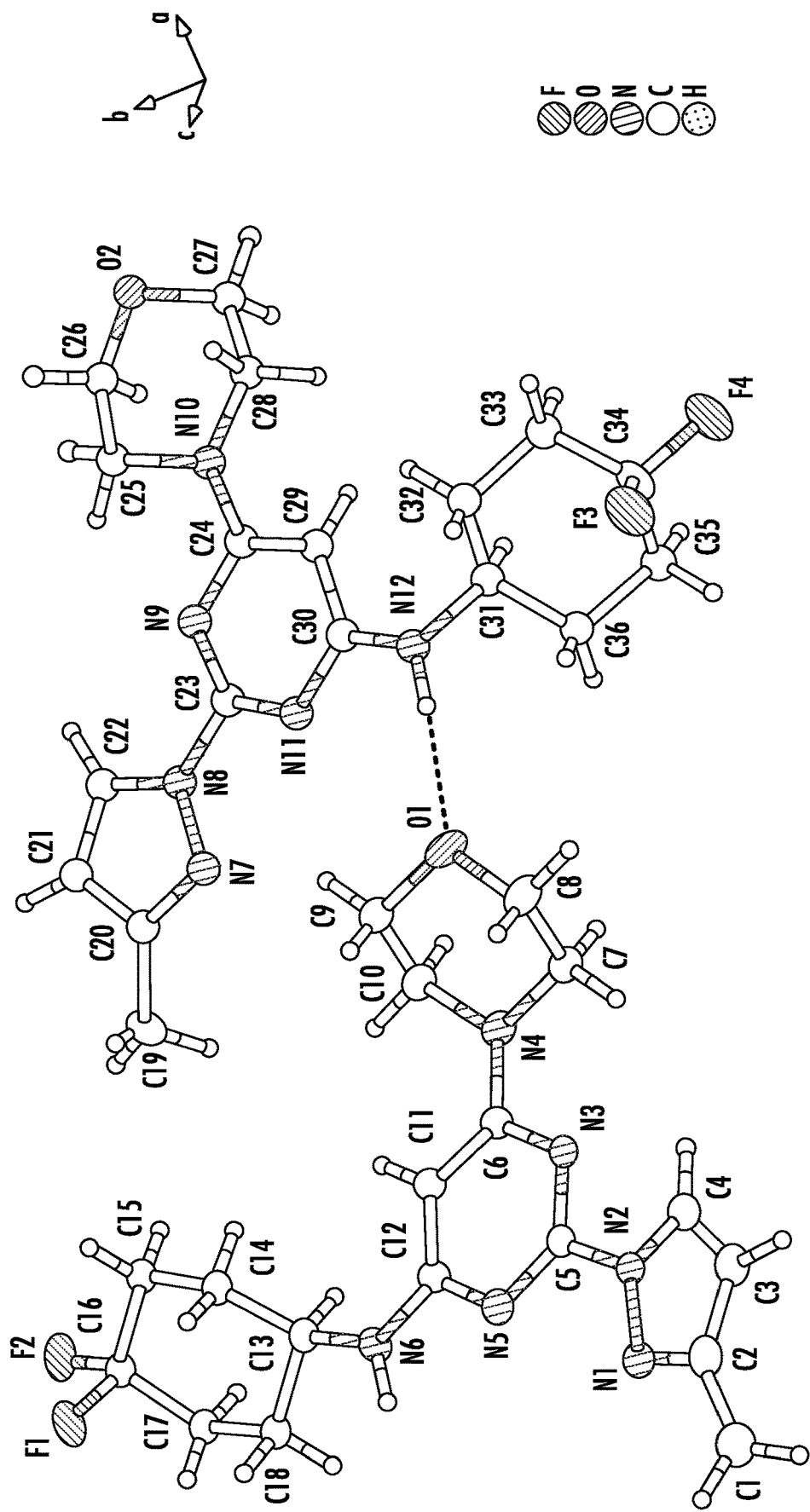
FIG. 3 depicts single x-ray diffraction (SCXRD) analyses of the crystal structure of Form B: A-E the Oak Ridge Thermal Ellipsoid Plot (ORTEP) structural illustrations of 3A the asymmetric unit of Form B single crystal, 3B the asymmetric unit of Form B single crystal consisting of two Compound 1 molecules, 3C the unit cell of Form B single crystal consisting of eight Compound 1 molecules, 3D hydrogen bonds in the Form B single crystal structure, and 3E the 3D packing of the unit cell viewed along c-axis in Form B single crystal; and 3F calculated and experimental XRPD patterns of Form B.
Figure 3B:
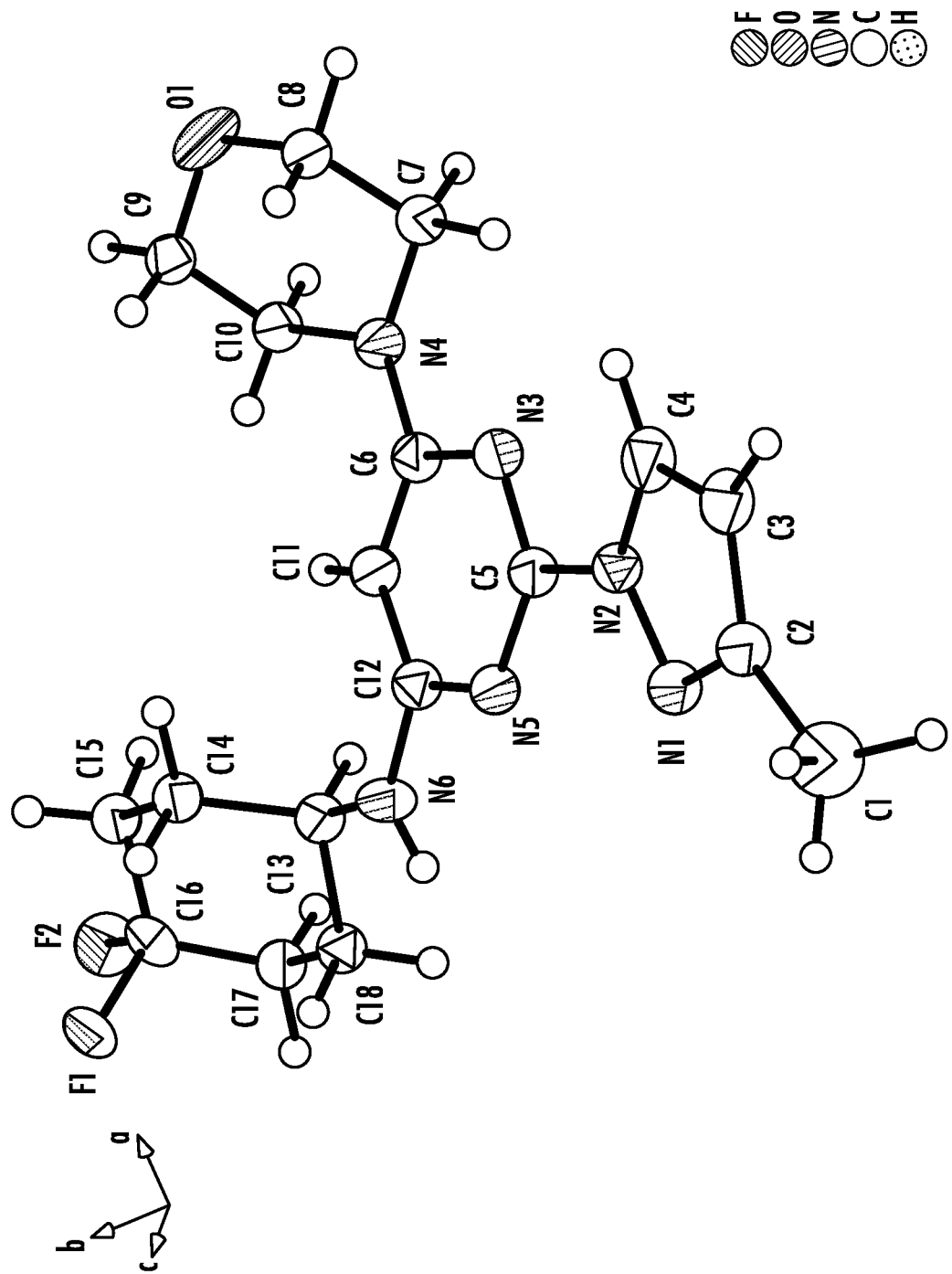
Figure 3C:
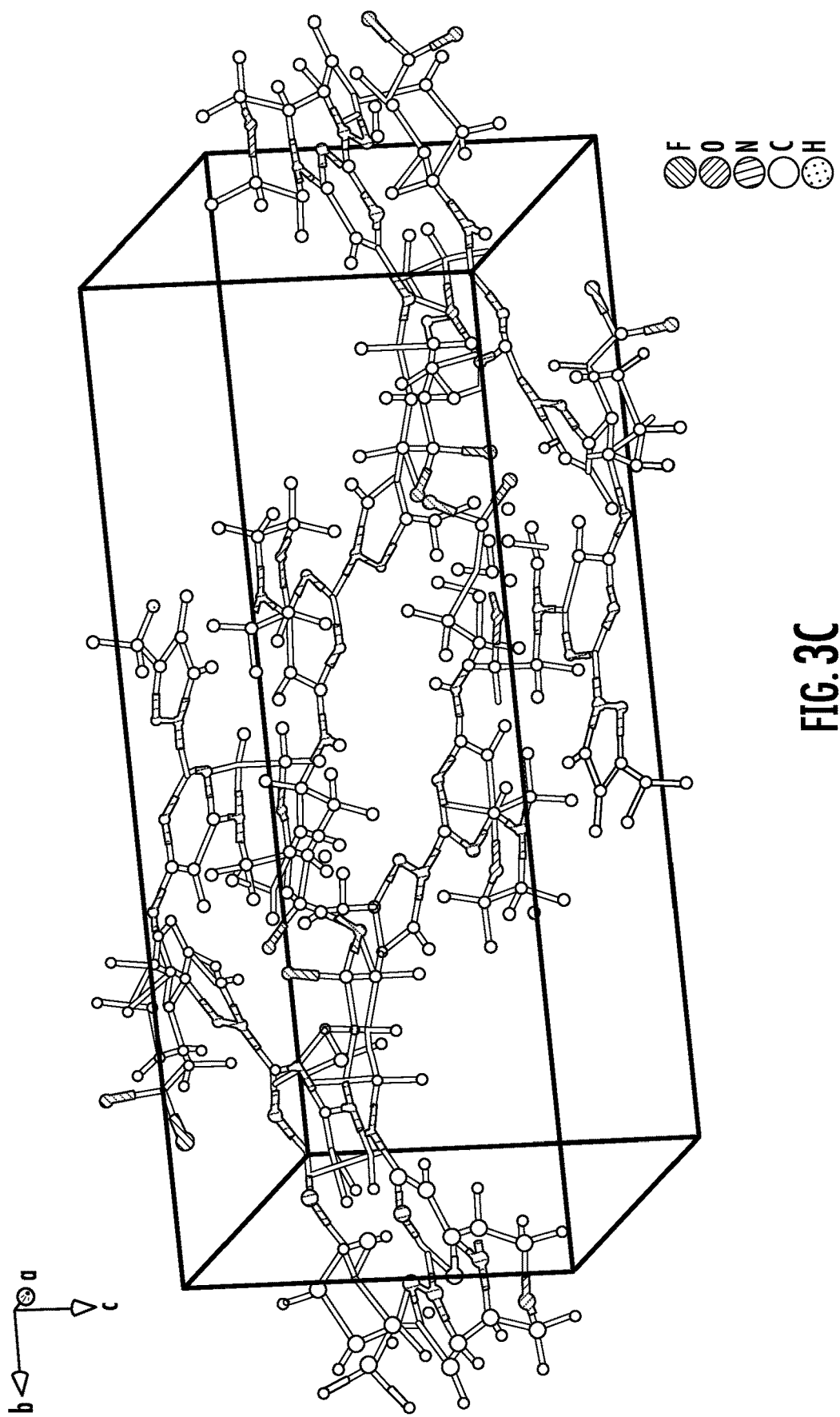
Figure 3D:
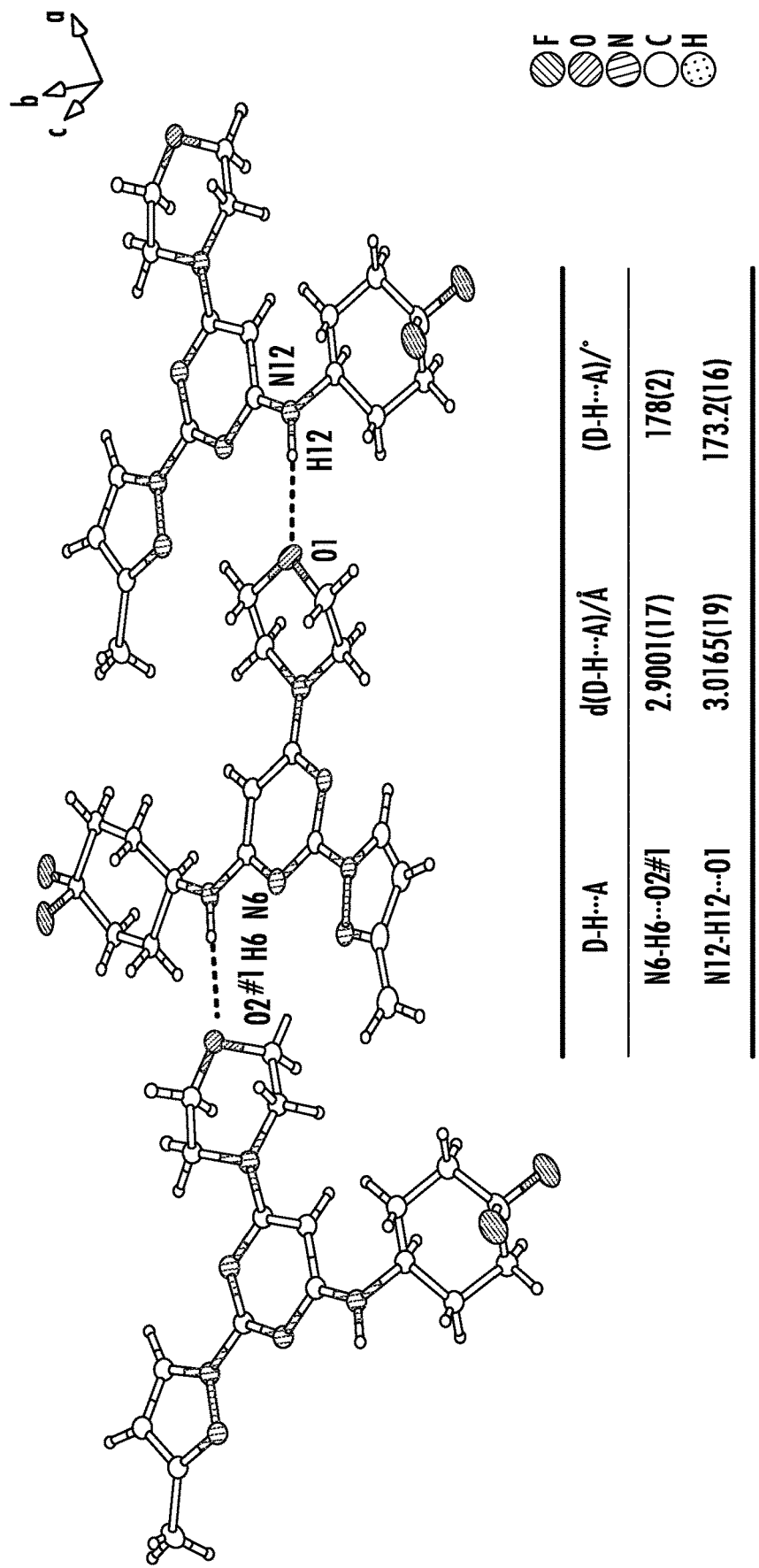
Figure 3E:
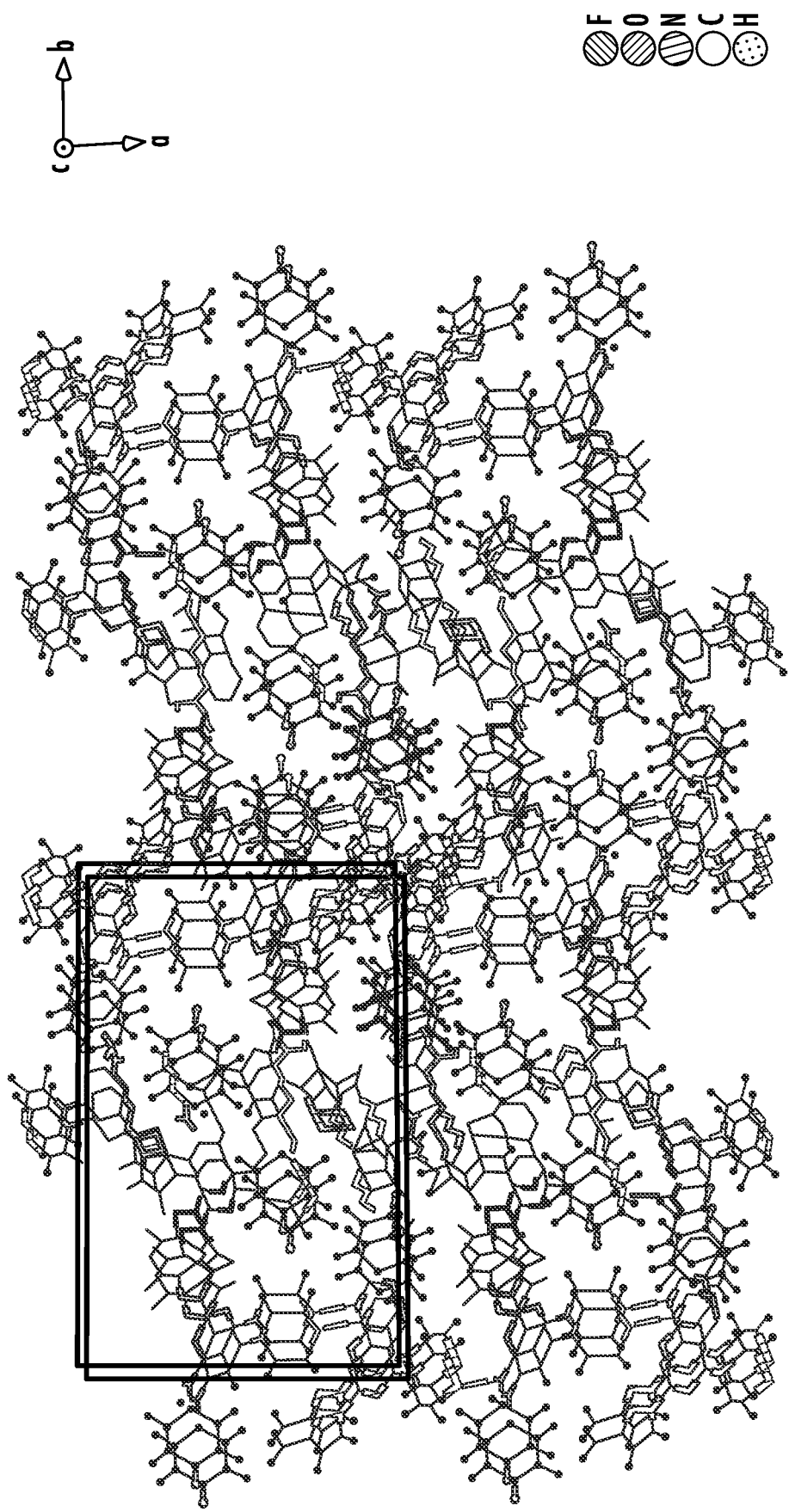
Figure 3F:
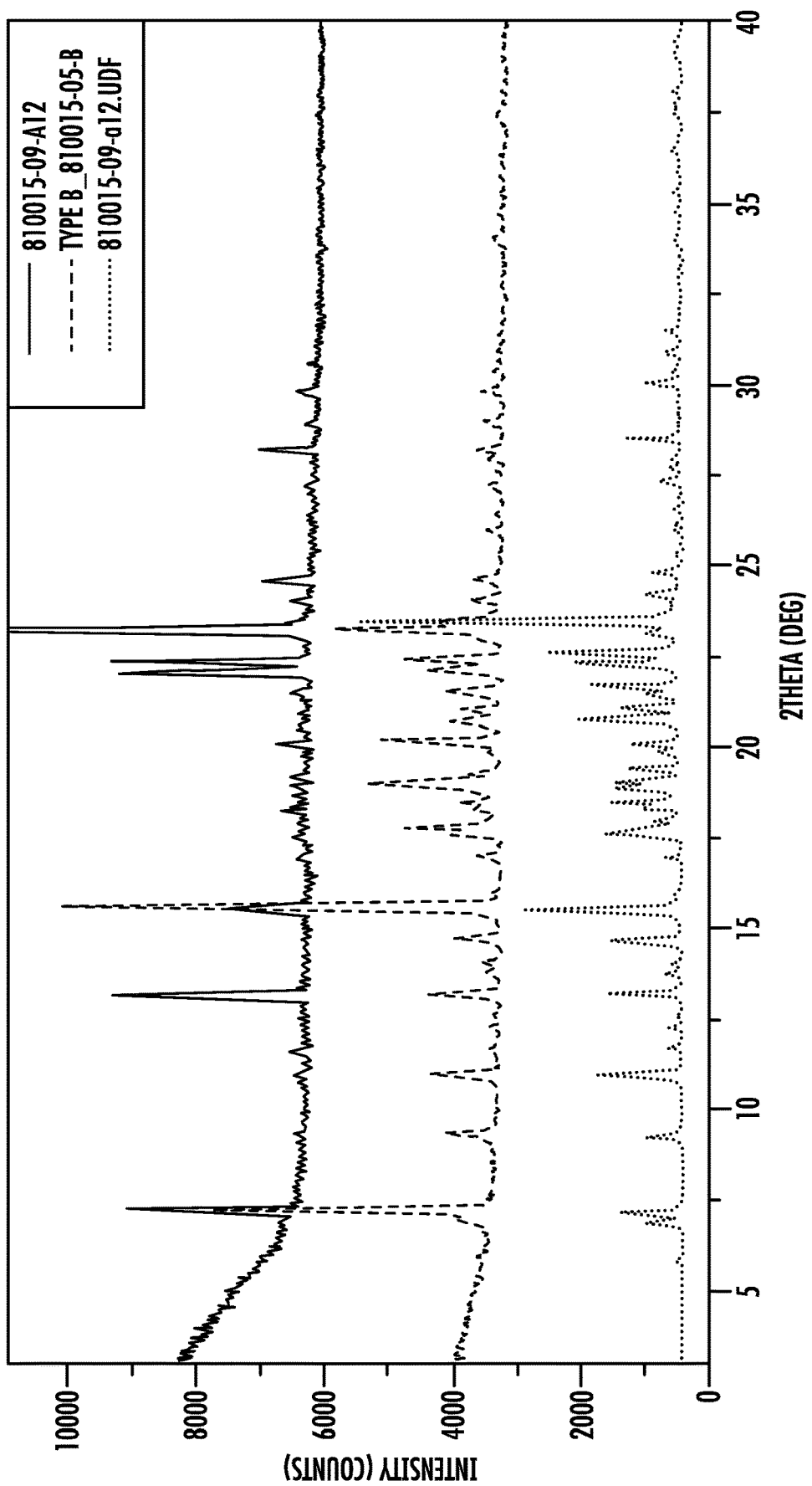

The crystal structure of Form B at the atomic and molecular level was determined by SCXRD (see FIG. 3), using the sample obtained by slow evaporation from ACN/H2O (1:1, v/v) solution at RT. The SCXRD analysis revealed that the crystal adopted the Monoclinic crystal system and P2₁/c space group with a=15.1466(2) Å, b=24.6770(4) Å, c=9.87220(17) Å, α=90°, β=94.4397(15)°, γ=90°, V=3678.89(10) Å³. The asymmetric unit of the Form B single crystal (FIG. 3A) consisted of two Compound 1 molecules (FIG. 3B), suggesting the crystal was an anhydrate. The unit cell of the Form B single crystal consisted of eight Compound 1 molecules (FIG. 3C). FIG. 3D showed the classic hydrogen bonds and FIG. 3E showed the 3D packing of the unit cell viewed along c-axis in the Form B single crystal structure. The calculated XRPD from the single crystal structure data was consistent with the experimental XRPD of Form B (FIG. 3F).

TABLE 16

XRPD of single crystalline Form B

| Pos. [°2Th.] | d-spacing [Å] | Rel. Int. [%] |
|---|---|---|
| 7.156134 | 12.35308 | 60.27 |
| 9.227475 | 9.58425 | 10.66 |
| 10.886250 | 8.12731 | 15.13 |
| 11.526900 | 7.67700 | 1.49 |
| 12.177290 | 7.26840 | 1.69 |
| 13.094060 | 6.76149 | 15.96 |
| 13.671450 | 6.47721 | 3.21 |
| 13.960340 | 6.34381 | 4.14 |
| 14.600230 | 6.06719 | 10.17 |
| 15.476650 | 5.72553 | 100.00 |
| 16.888730 | 5.24986 | 5.05 |
| 17.665540 | 5.02072 | 21.50 |
| 18.364500 | 4.83118 | 8.57 |
| 18.878580 | 4.70077 | 30.47 |
| 19.146590 | 4.63557 | 6.78 |
| 20.050540 | 4.42857 | 26.55 |
| 20.621050 | 4.30732 | 11.03 |
| 20.926090 | 4.24522 | 8.78 |
| 21.425230 | 4.14743 | 13.13 |
| 21.995030 | 4.04126 | 16.58 |
| 22.304330 | 3.98592 | 21.56 |
| 23.156060 | 3.84120 | 37.18 |
| 23.974810 | 3.71184 | 7.00 |
| 24.534800 | 3.62838 | 6.46 |
| 25.202700 | 3.53371 | 0.89 |
| 25.891670 | 3.44122 | 2.86 |
| 26.353470 | 3.38196 | 1.15 |
| 27.119010 | 3.28821 | 3.15 |
| 28.121280 | 3.17325 | 5.38 |
| 28.886390 | 3.09092 | 3.71 |
| 29.716040 | 3.00648 | 4.36 |
| 33.910100 | 2.64362 | 2.47 |
| 34.673120 | 2.58718 | 1.22 |
| 35.183730 | 2.55079 | 1.34 |
| 37.334850 | 2.40862 | 1.78 |
| 38.910120 | 2.31466 | 0.72 |

GMP Manufacture of Single Crystalline Form B Form

Form A (6.53 Kg) was dissolved in 2-MeTHF and the solution was heated to 70° C. Over the course of approximately 80 minutes, heptane (52.79 L, 35.90 kg, 8 volumes) was slowly charged to the reactor via an addition funnel. Agitation was momentarily paused, allowing water that had separated out of solution to settle on the bottom of the reactor. The water was drained (1.04 L), and agitation resumed for not less than 30 minutes. Over a span of 3 hours, the reactor jacket temperature ramped down (linear) from 70° C. to 60° C. During this period, the crystallization of solids was observed (internal process temperature was approximately 67° C.). The temperature was held at 60° C. for a duration of 3 hours, followed by a linear ramped-down over a 3-hour period from 60° C. to 20° C. The solids were transferred from the reactor to a 24" polypropylene table-top filter funnel. The product was washed two times with polish-filtered heptane (32.69 L, 22.23 kg, 5 volumes) for a total wash of 10 volumes. The desired Form B product was transferred to Teflon lined drying trays, and dried under vacuum at 50° C. with a nitrogen bleed, until constant mass was achieved. Drying occurred over the course of 4 days, yielding the desired product, Form B, as a light-yellow solid in 82% yield.

Example 2: Preparation of Single Crystalline Form C

Figure 5:
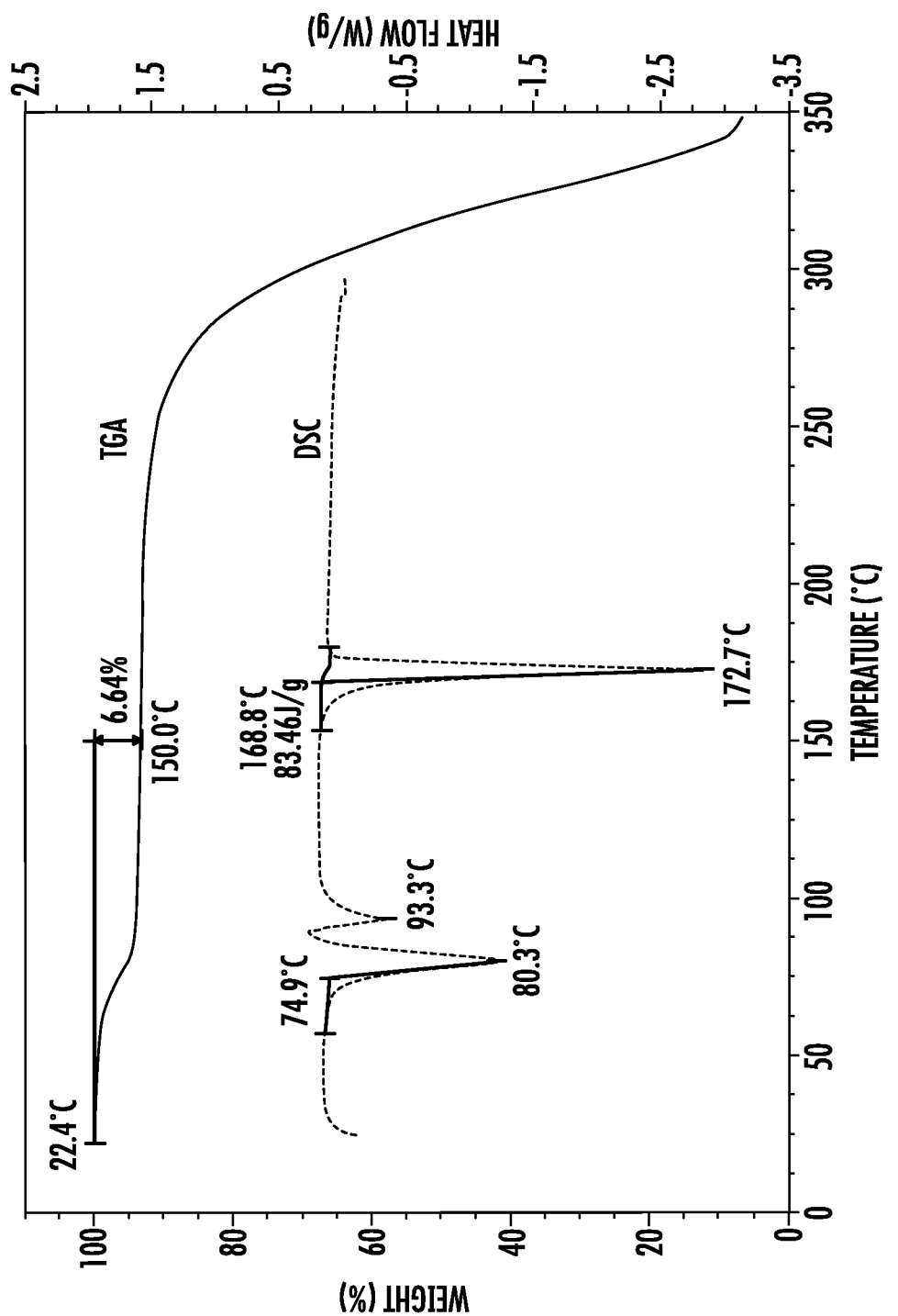
FIG. 5 depicts the combined thermogravimetric analysis (TGA) thermogram and differential scanning calorimetry (DSC) thermogram for crystalline Form C.

Form C was obtained by slow evaporation from an IPA solution at RT. Form C showed a strong, unique XRPD pattern with sharp peaks and a relatively flat baseline, indicative of a crystalline material (see FIG. 4 and Table 17). Form C showed a TGA curve with a step weight loss of 6.6% up to 150° C., as well as a DSC curve with three endotherms at 74.9° C. and 168.8° C. (onset temperatures) and 93.3° C. (peak temperature) (FIG. 5). Form C was found to be IPA solvate that converted to anhydrate Form B after heated to 110° C. or stored at RT for 8 days, by $^1$H solution NMR and XRPD analyses.

TABLE 17

XRPD of single crystalline Form C

| Pos. [°2Th.] | d-spacing [Å] | Rel. Int. [%] |
|---|---|---|
| 4.229768 | 20.89073 | 34.39 |
| 4.544583 | 19.44426 | 4.34 |
| 8.464246 | 10.44668 | 82.24 |
| 9.096947 | 9.72147 | 1.17 |
| 9.698006 | 9.12027 | 4.74 |
| 10.416890 | 8.49242 | 5.24 |
| 13.083840 | 6.76675 | 1.34 |
| 13.746750 | 6.44190 | 3.71 |
| 15.229290 | 5.81797 | 0.90 |
| 17.041950 | 5.20300 | 100.00 |
| 17.686770 | 5.01474 | 2.32 |
| 18.244950 | 4.86256 | 2.38 |
| 18.573650 | 4.77725 | 3.89 |
| 19.278020 | 4.60426 | 1.56 |
| 19.815810 | 4.48050 | 1.82 |
| 20.151740 | 4.40656 | 9.52 |
| 21.367220 | 4.15856 | 59.09 |
| 22.459880 | 3.95866 | 4.15 |
| 24.109100 | 3.69147 | 2.07 |

Example 3: Preparation of Single Crystalline Form D

Figure 8:
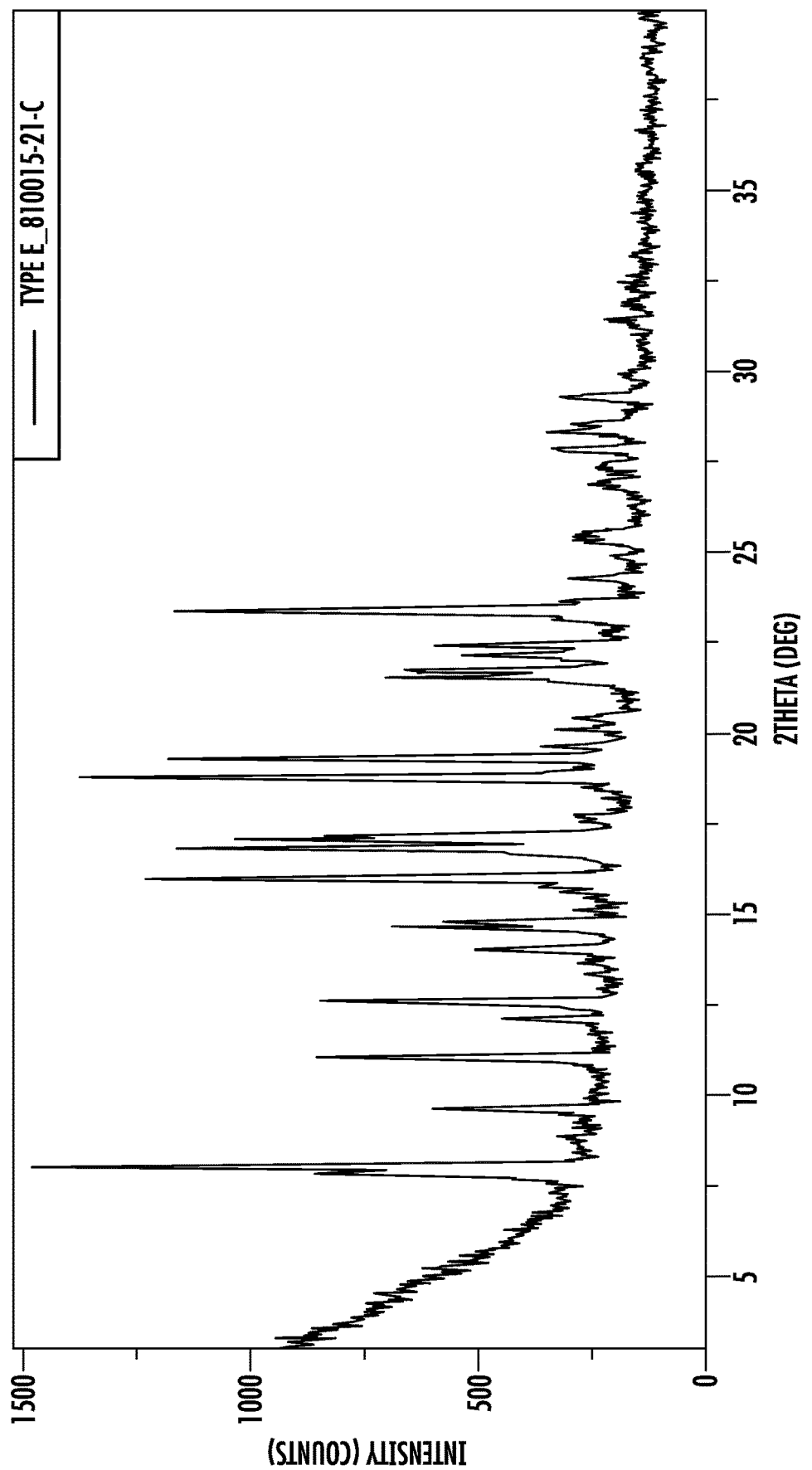
FIG. 8 depicts an x-ray powder diffraction (XRPD) pattern for crystalline Form E.

Form D was obtained via slow evaporation from EtOH solution at RT. Form D showed a strong, unique XRPD pattern with sharp peaks and a relatively flat baseline, indicative of a crystalline material (see FIG. 7 and Table 18). Form D showed a TGA curve with a step weight loss of 8.8% up to 150° C. as well as a DSC curve with two endotherms at 69.8° C. and 169.7° C. (onset temperatures) and an exotherm at 88.5° C. (peak temperature) (FIG. 8). Form D was found to be EtOH solvate that converted to anhydrate Form B after stored at RT for a month, by $^1$H solution NMR and XRPD analyses.

TABLE 18

XRPD of single crystalline Form D

| Pos. [°2Th.] | d-spacing [Å] | Rel. Int. [%] |
|---|---|---|
| 4.898084 | 18.04170 | 22.81 |
| 9.870212 | 8.96153 | 47.21 |
| 11.099930 | 7.97133 | 52.87 |
| 14.809040 | 5.98211 | 13.93 |
| 17.394970 | 5.09820 | 100.00 |
| 21.310910 | 4.16942 | 31.74 |
| 22.244260 | 3.99654 | 68.72 |
| 24.792990 | 3.59117 | 14.08 |
| 30.118660 | 2.96721 | 8.12 |

Example 4: Preparation of Single Crystalline Form E

Figure 9:
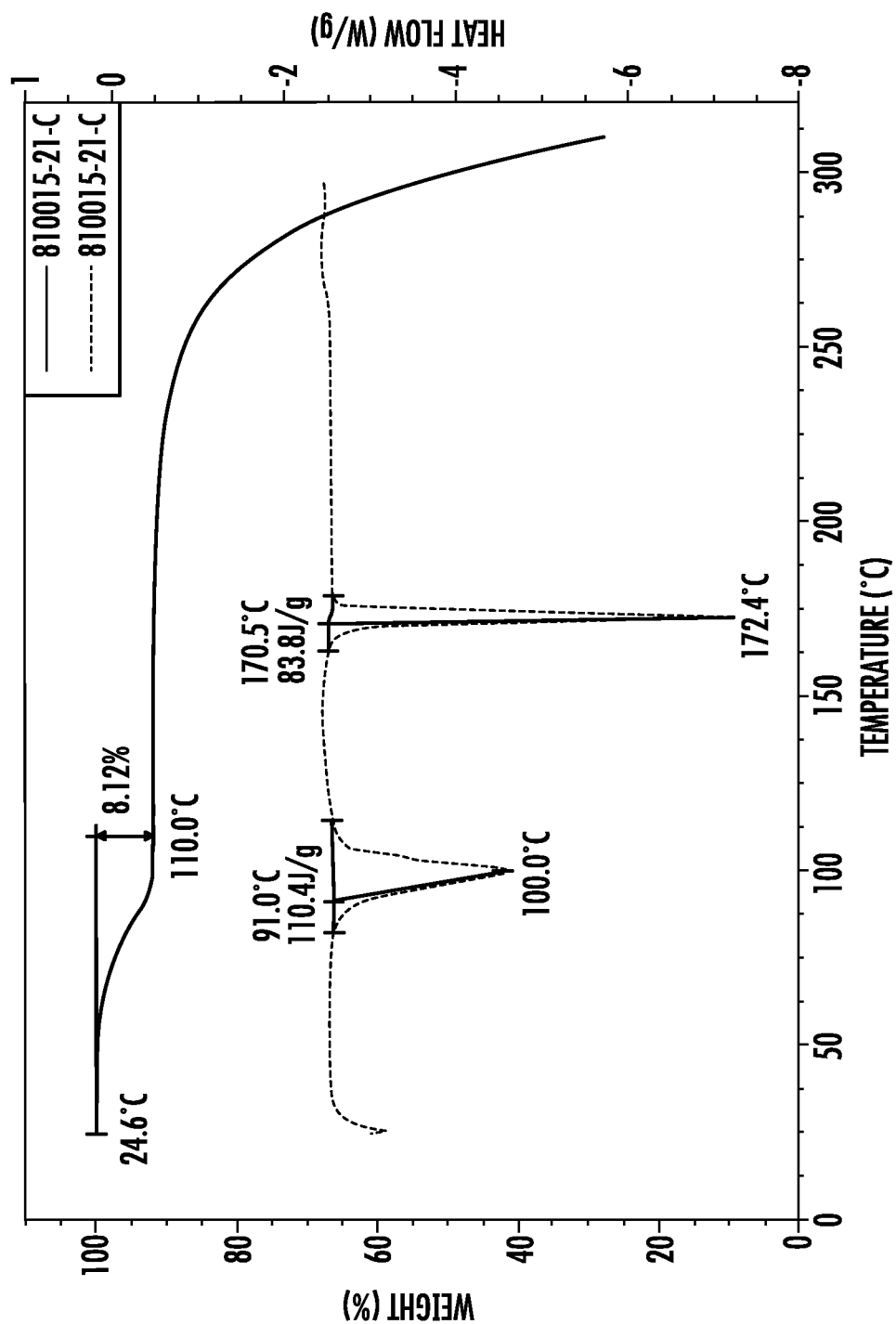
FIG. 9 depicts the combined thermogravimetric analysis (TGA) thermogram and differential scanning calorimetry (DSC) thermogram for crystalline Form E.

Form E sample was obtained via placing the Form A starting material in a chamber full of volatile MeOH solvent at RT for 8 days. Form E showed a strong, unique XRPD pattern with sharp peaks and a relatively flat baseline, indicative of a crystalline material (see FIG. 8 and Table 19). Form E showed a TGA curve with a step weight loss of 8.1% up to 110° C., as well as a DSC curve with two endotherms at 91.0° C. and 170.5° C. (onset temperatures) (FIG. 9). Form E was found to be MeOH solvate that converted to anhydrate Form B after heated to 130° C., by $^1$H solution NMR and XRPD analyses.

TABLE 19

XRPD of single crystalline Form E

| Pos. [°2Th.] | d-spacing [Å] | Rel. Int. [%] |
|---|---|---|
| 3.184209 | 27.74763 | 17.23 |
| 7.996826 | 11.05621 | 77.65 |
| 9.638795 | 9.17616 | 29.59 |
| 11.045390 | 8.01056 | 41.70 |
| 12.115180 | 7.30552 | 18.93 |
| 12.591690 | 7.03010 | 50.90 |
| 14.056210 | 6.30076 | 24.99 |
| 14.688860 | 6.03078 | 22.42 |
| 15.994650 | 5.54125 | 86.61 |
| 16.815980 | 5.27241 | 70.23 |
| 17.113930 | 5.18128 | 57.68 |
| 17.670550 | 5.01931 | 6.61 |
| 18.797420 | 4.72088 | 100.00 |
| 19.340050 | 4.58963 | 82.07 |
| 19.630910 | 4.52228 | 15.29 |
| 20.101930 | 4.41737 | 10.46 |
| 21.535870 | 4.12637 | 38.06 |
| 21.749990 | 4.08623 | 41.36 |
| 22.153240 | 4.01276 | 31.02 |
| 22.420710 | 3.96549 | 36.04 |
| 23.381110 | 3.80473 | 84.99 |
| 24.258590 | 3.66906 | 9.81 |
| 25.451220 | 3.49977 | 9.70 |
| 26.896600 | 3.31489 | 8.26 |
| 27.818180 | 3.20713 | 15.04 |
| 28.346960 | 3.14850 | 14.69 |
| 29.276680 | 3.05060 | 15.02 |
| 31.408110 | 2.84827 | 5.19 |

Example 5: Preparation of Single Crystalline Form F

Figure 11:
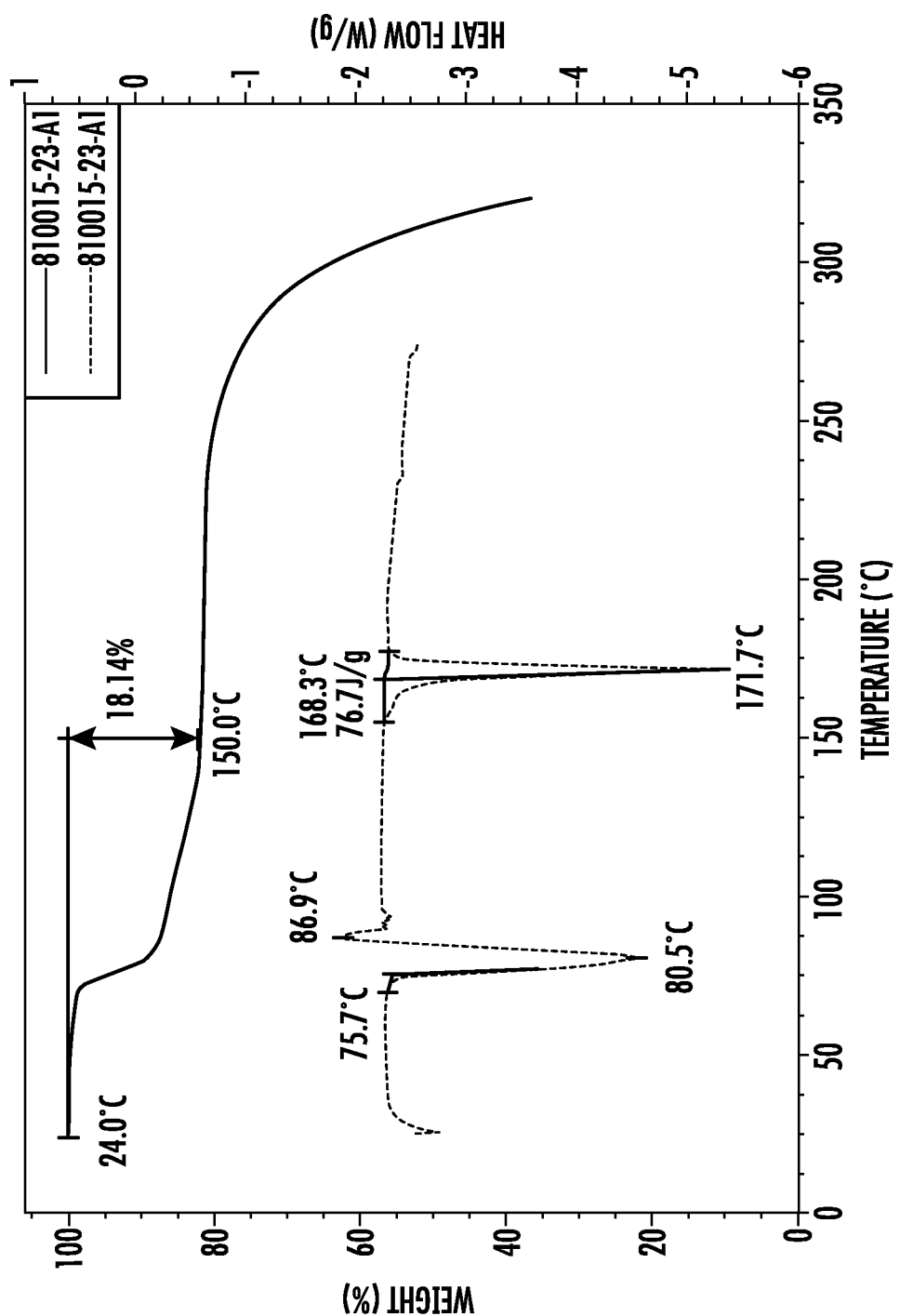
FIG. 11 depicts the combined thermogravimetric analysis (TGA) thermogram and differential scanning calorimetry (DSC) thermogram for crystalline Form F.

Form F was obtained by evaporation of DCM solution (100 mg scale) at RT for 1 day. Form F showed a strong, unique XRPD pattern with sharp peaks and a relatively flat baseline, indicative of a crystalline material (see FIG. 10 and Table 20). Form F showed a TGA curve with a step weight loss of 18.1% up to 150° C., as well as a DSC curve with two endotherms at 75.7° C. and 168.3° C. (onset temperatures) and an exotherm at 86.9° C. (peak temperature) (FIG. 11). Form F was found to be DCM solvate that converted to anhydrate Form B after heated to 120° C., by $^1$H solution NMR and XRPD analyses.

TABLE 20

XRPD of single crystalline Form F

| Pos. [°2Th.] | d-spacing [Å] | Rel. Int. [%] |
|---|---|---|
| 3.398548 | 25.99811 | 6.08 |
| 7.084709 | 12.47746 | 59.40 |
| 10.164230 | 8.70296 | 3.25 |
| 12.247130 | 7.22710 | 3.22 |
| 16.098370 | 5.50578 | 1.73 |
| 17.451150 | 5.08192 | 7.97 |
| 17.940350 | 4.94443 | 9.62 |
| 18.813090 | 4.71698 | 10.78 |
| 19.260910 | 4.60831 | 3.12 |
| 20.459110 | 4.34105 | 7.07 |
| 21.387790 | 4.15461 | 100.00 |
| 22.149230 | 4.01348 | 12.73 |
| 22.973100 | 3.87137 | 3.37 |
| 23.430970 | 3.79675 | 3.58 |
| 24.402940 | 3.64768 | 11.80 |
| 24.918290 | 3.57340 | 6.59 |
| 25.226130 | 3.53048 | 7.06 |
| 26.994900 | 3.30304 | 3.89 |
| 28.822940 | 3.09758 | 9.85 |
| 29.317950 | 3.04640 | 2.24 |
| 30.744450 | 2.90822 | 1.17 |
| 32.083800 | 2.78981 | 1.13 |

Example 6: Preparation of the Amorphous Form of Compound 1

Figure 13:
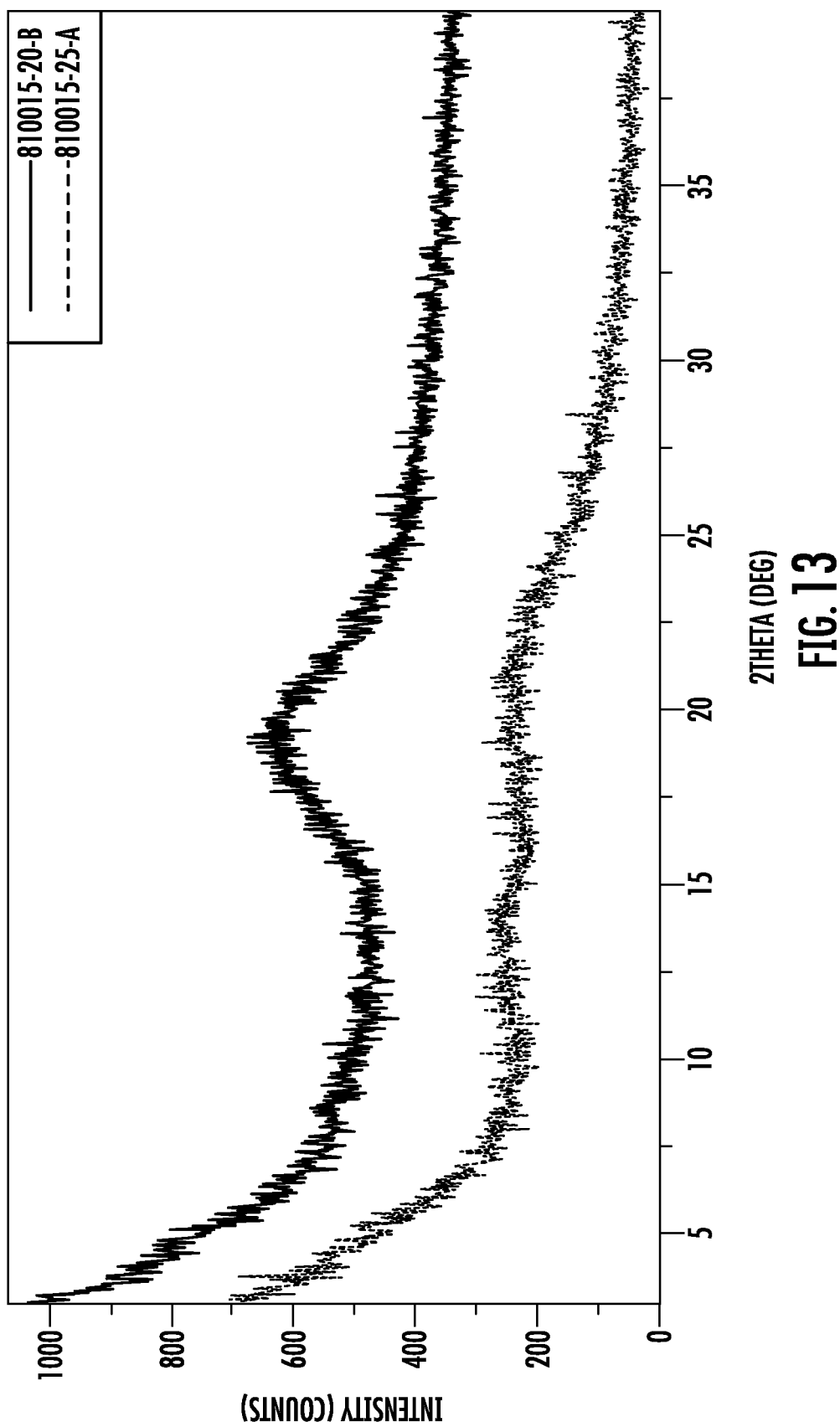
FIG. 13 depicts the x-ray powder diffraction (XRPD) patterns for amorphous Form of Compound 1.
Figure 14:
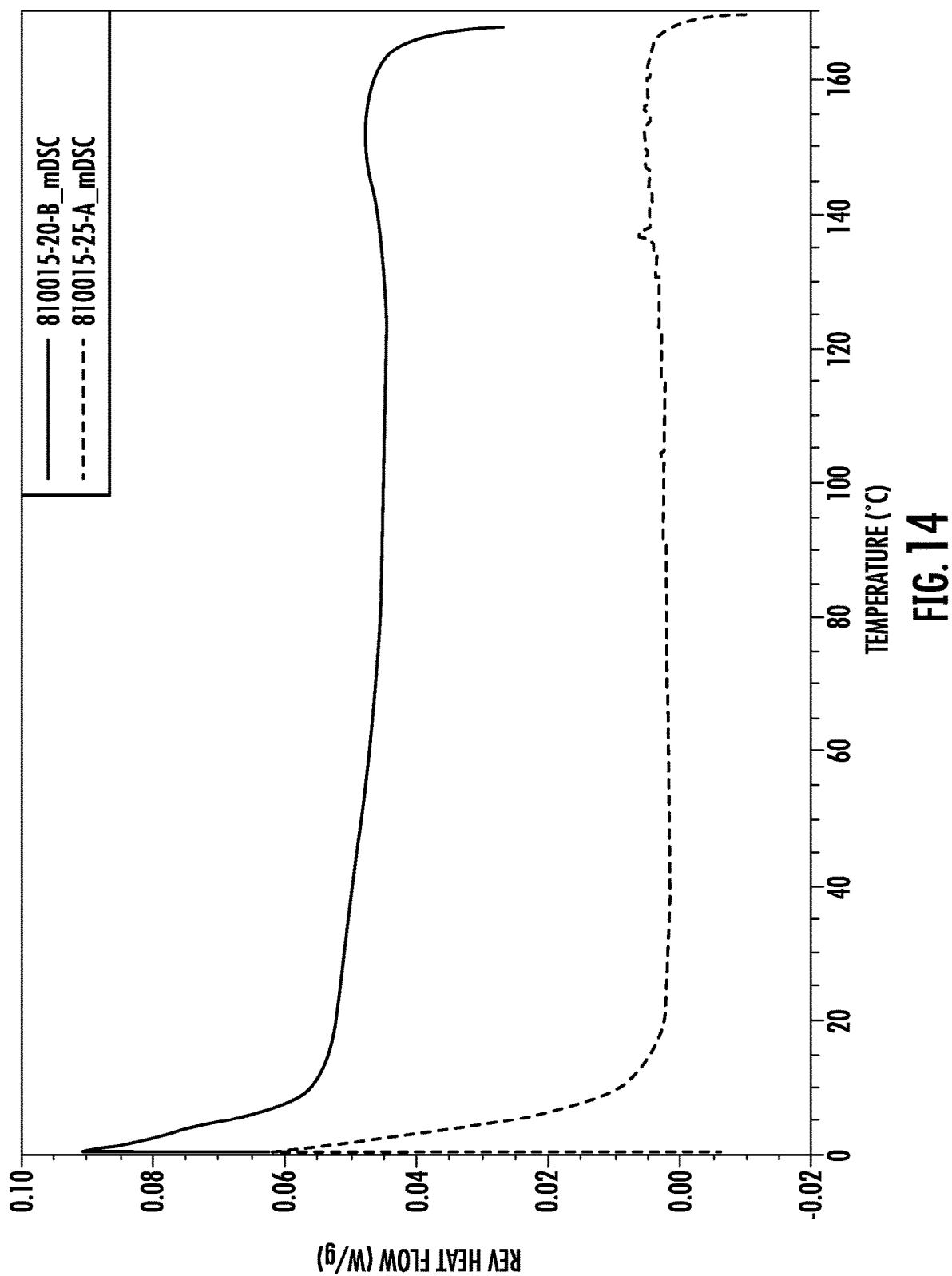
FIG. 14 depicts the differential scanning calorimetry (DSC) thermograms for amorphous Form of Compound 1.

Two batches of the amorphous Form (50-mg and 200-mg scale) were prepared via evaporation of DCM solution of the Form A starting material at RT. For the 200-mg batch, 202.0 mg of Form A was weighed into a 3-mL vial followed by the addition of 1 mL of DCM to dissolve the solids. The solution was filtered using a PTFE membrane (pore size of 0.45 µm) and the filtrate was subject to evaporate in vacuum at 30° C. XRPD and mDSC results are shown in FIG. 13 and FIG. 14. No glass transition temperature (Tg) was observed for either batch of the amorphous form.

The invention claimed is:

1. A single crystalline Form B of a compound having structural formula 1:

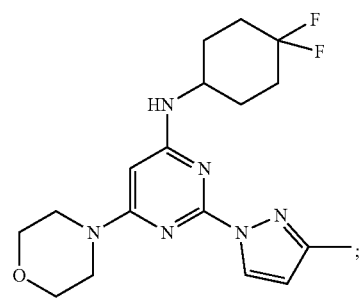

wherein the crystalline form is characterized by at least three x-ray powder diffraction peaks at 2 Θ angles selected from 7.2°, 17.7°, 20.1°, 23.3°, and 23.2°.

2. The single crystalline Form B of claim 1, wherein the crystalline form is characterized by at least four x-ray powder diffraction peaks at 2Θ angles selected from 7.2°, 15.5°, 17.7°, 18.9°, 20.1°, 22.3°, and 23.2°.

3. The single crystalline Form B of claim 1, wherein the crystalline form is characterized by at least five x-ray powder diffraction peaks at 2Θ angles selected from 7.2°, 15.5°, 17.7°, 18.9°, 20.1°, 22.3°, and 23.2°.

4. The single crystalline Form B of claim 1, wherein the crystalline form is characterized by at least six x-ray powder diffraction peaks at 2Θ angles selected from 7.2°, 15.5°, 17.7°, 18.9°, 20.1°, 22.3°, and 23.2°.

5. The single crystalline Form B of claim 1, wherein the crystalline form is characterized by x-ray powder diffraction peaks at 2Θ angles selected from 7.2°, 15.5°, 17.7°, 18.9°, 20.1°, 22.3°, and 23.2°.

6. The single crystalline Form B of claim 1, wherein the crystalline form is characterized by x-ray powder diffraction peaks at 2Θ angles selected from 7.2°, 9.2°, 10.9°, 13.1°, 14.6°, 15.5°, 17.7°, 18.9°, 20.1°, 20.6°, 21.4°, 22.0°, 22.3°, and 23.2°.

7. The single crystalline Form B of claim 1, wherein the crystalline form is characterized by x-ray powder diffraction peaks at 2Θ angles selected from 7.2°, 9.2°, 10.9°, 11.5°, 12.2°, 13.1°, 13.7°, 14.0°, 14.6°, 15.5°, 16.9°, 17.7°, 18.4°, 18.9°, 19.1°, 20.1°, 20.6°, 20.9°, 21.4°, 22.0°, 22.3°, 23.2°, 24.0°, 24.5°, 25.2°, 25.9°, 26.4°, 27.1°, 28.1°, 28.9°, 29.7°, 33.9°, 34.7°, 35.2°, 37.3°, and 38.9°.

8. A single crystalline Form C, single crystalline Form D, single crystalline Form E, or single crystalline Form F of a compound having structural formula 1:

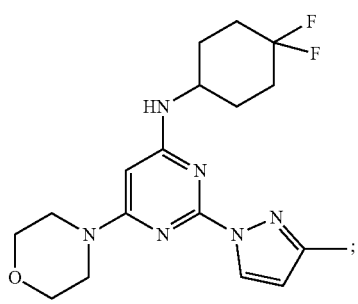

(1)

wherein the single crystalline Form C is characterized by at least three, at least four, five, x-ray powder diffraction peaks at 2 Θ angles selected from 4.2°, 8.5°, 17.00, 20.20, and 21.40; wherein the single crystalline Form D is characterized by at least three, at least four, at least five, at least six, or at least seven x-ray powder diffraction peaks at 2 Θ angles selected from 4.90, 99°, 11.10, 17.40, 21.30, 22.20, and 24.8°; wherein the single crystalline Form E is characterized by at least three, at least four, at least five, at least six, or at least seven x-ray powder diffraction peaks at 2Θ angles selected from 8.0°, 16.00, 16.80, 17.10, 18.80, 19.30, and 23.4°; and wherein the single crystalline Form F is characterized by at least three, at least four, at least five, at least six, or at least seven x-ray powder diffraction peaks at 2 Θ angles selected from 7.1°, 17.90, 18.80, 21.40, 22.10, 24.40, and 28.80.

9. A pharmaceutical composition comprising the crystalline Form B of claim 1; and a pharmaceutically acceptable carrier.

10. A method of treating a disease or condition responsive to modulation of the small conductance calcium-activated potassium channel (SK channel) in a subject comprising the step of administering to the subject a therapeutically effective amount of the crystalline Form B of claim 1.

11. A method of preparing the crystalline Form B of claim 1, said method comprising:
dissolving Form A in 2-MeTHF at elevated temperature to form a solution;
adding heptane to the solution; and
reducing the temperature of the solution, thereby precipitating Form B.

12. A pharmaceutical composition comprising the crystalline Form C, Form D, Form E, or Form F of claim 8, and a pharmaceutically acceptable carrier.

13. A method of treating a disease or condition responsive to modulation of the small conductance calcium-activated potassium channel (SK channel) in a subject comprising the step of administering to the subject a therapeutically effective amount of the crystalline Form C, Form D, Form E, or Form F of claim 8.

* * * * *